(12) United States Patent
Wang et al.

(10) Patent No.: US 11,547,490 B2
(45) Date of Patent: Jan. 10, 2023

(54) SYSTEMS AND METHODS FOR NAVIGATION IN IMAGE-GUIDED MEDICAL PROCEDURES

(71) Applicant: INTUITIVE SURGICAL OPERATIONS, INC., Sunnyvale, CA (US)

(72) Inventors: Bai Wang, Palo Alto, CA (US); Tao Zhao, Sunnyvale, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 217 days.

(21) Appl. No.: 16/349,073

(22) PCT Filed: Dec. 7, 2017

(86) PCT No.: PCT/US2017/065162
§ 371 (c)(1),
(2) Date: May 10, 2019

(87) PCT Pub. No.: WO2018/106950
PCT Pub. Date: Jun. 14, 2018

(65) Prior Publication Data
US 2019/0350659 A1   Nov. 21, 2019

Related U.S. Application Data

(60) Provisional application No. 62/431,696, filed on Dec. 8, 2016.

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61B 34/25* (2016.02); *A61B 34/35* (2016.02);
(Continued)

(58) Field of Classification Search
CPC ... A61B 34/20; A61B 34/10; A61B 2034/107; A61B 2034/2061; A61B 2034/105;
(Continued)

(56) References Cited

U.S. PATENT DOCUMENTS 5,611,025 A * 3/1997 Lorensen ............. G09B 23/285
345/419
5,661,025 A * 3/1997 Lorensen ................. A61B 8/13
395/119
(Continued)

FOREIGN PATENT DOCUMENTS

| CN | 101443819 A | 5/2009 |
| CN | 104050313 A | 9/2014 |

(Continued)

OTHER PUBLICATIONS

Extended European Search Report for Application No. EP17879065.5 dated Jun. 18, 2020, 9 pages.
(Continued)

*Primary Examiner* — Sean D Mattson
*Assistant Examiner* — Michael Yiming Fang
(74) *Attorney, Agent, or Firm* — Haynes and Boone, LLP

(57) ABSTRACT

Medical imaging systems and methods are provided herein that provide for navigation and procedure planning without segmentation. A method comprises receiving, by a medical imaging system having at least one processing device, three-dimensional image data of a patient anatomy. The method also comprises filtering the three-dimensional data to display a portion of the three-dimensional image data that
(Continued)

is associated with the patient anatomy and receiving, at the processing device, input from an operator input device. The input comprises navigational directions for virtual movement within a space defined by the three-dimensional image data. The method also includes tracking the virtual movement, defining a tracked pathway based on the tracked virtual movement, and generating a model of the patient anatomy based on the tracked pathway. The model of the patient anatomy is a line model including one or more lines based on the tracked pathway.

19 Claims, 21 Drawing Sheets

(51) Int. Cl.
 *A61B 34/00* (2016.01)
 *A61B 34/35* (2016.01)
 *A61B 6/03* (2006.01)
 *G16H 30/40* (2018.01)

(52) U.S. Cl.
 CPC ......... *A61B 6/032* (2013.01); *A61B 2034/105* (2016.02); *A61B 2034/2051* (2016.02); *A61B 2034/2055* (2016.02); *A61B 2034/2057* (2016.02); *A61B 2034/2061* (2016.02); *A61B 2034/2065* (2016.02); *A61B 2034/254* (2016.02); *G16H 30/40* (2018.01)

(58) Field of Classification Search
 CPC ............ A61B 34/25; A61B 2034/2065; A61B 2034/254; A61B 34/35; A61B 6/032; A61B 2034/2051; A61B 2034/2055; A61B 2034/2057; A61B 90/00; A61B 8/0841; A61B 6/12; G16H 30/40
 See application file for complete search history.

(56) References Cited

U.S. PATENT DOCUMENTS

| | | | |
|---|---|---|---|
| 6,345,112 B1* | 2/2002 | Summers ............... | G06V 20/64 |
| | | | 382/128 |
| 6,380,732 B1 | 4/2002 | Gilboa et al. | |
| 6,389,187 B1 | 5/2002 | Greenaway et al. | |
| 7,316,681 B2 | 1/2008 | Madhani et al. | |
| 7,772,541 B2 | 8/2010 | Froggatt et al. | |
| 8,900,131 B2 | 12/2014 | Chopra et al. | |
| 9,129,359 B2* | 9/2015 | Averbuch ............... | G06T 17/00 |
| 9,259,274 B2 | 2/2016 | Prisco et al. | |
| 9,452,276 B2 | 9/2016 | Duindam et al. | |
| 9,639,666 B2* | 5/2017 | Baker ..................... | G16H 50/50 |
| 9,770,216 B2* | 9/2017 | Brown .................... | A61B 6/5247 |
| 10,249,036 B2* | 4/2019 | Holsing ................... | A61B 5/7285 |
| 2006/0013523 A1 | 1/2006 | Childers et al. | |
| 2007/0092864 A1 | 4/2007 | Reinhardt et al. | |
| 2007/0276234 A1* | 11/2007 | Shahidi .................. | A61B 34/20 |
| | | | 600/437 |
| 2008/0214922 A1 | 9/2008 | Hartmann et al. | |
| 2009/0105579 A1 | 4/2009 | Garibaldi | |
| 2011/0107270 A1 | 5/2011 | Wang et al. | |
| 2013/0165854 A1* | 6/2013 | Sandhu ............ | A61B 17/00234 |
| | | | 604/95.01 |
| 2013/0223702 A1 | 8/2013 | Holsing et al. | |
| 2014/0188440 A1* | 7/2014 | Donhowe ............... | A61B 10/04 |
| | | | 703/1 |
| 2014/0221921 A1* | 8/2014 | Gilboa .................... | A61B 1/00 |
| | | | 604/95.04 |
| 2014/0282216 A1* | 9/2014 | Baker .................... | G06T 7/0012 |
| | | | 715/781 |
| 2016/0000302 A1* | 1/2016 | Brown ............... | A61B 1/00039 |
| | | | 600/103 |
| 2016/0061599 A1* | 3/2016 | Zeng ..................... | A61B 19/00 |
| 2016/0100773 A1 | 4/2016 | Ching et al. | |
| 2016/0166333 A1* | 6/2016 | Wang ...................... | A61B 90/11 |
| | | | 600/476 |
| 2016/0184013 A1* | 6/2016 | Brannan ................. | A61B 18/14 |
| | | | 600/424 |
| 2016/0192987 A1* | 7/2016 | Brannan ................. | A61B 34/20 |
| | | | 606/33 |
| 2018/0240237 A1 | 8/2018 | Donhowe et al. | |

FOREIGN PATENT DOCUMENTS

| | | | | |
|---|---|---|---|---|
| EP | 2779004 A1 | | 9/2014 | |
| EP | 2953532 A1 | | 12/2015 | |
| GB | 2416944 A | | 2/2006 | |
| WO | WO-2007126842 A2 | | 11/2007 | |
| WO | WO-2013080131 A1 | | 6/2013 | |
| WO | WO-2015148378 A1 | * | 10/2015 | ............ A61B 18/02 |
| WO | WO-2016191298 A1 | | 12/2016 | |
| WO | WO-2017030913 A2 | | 2/2017 | |

OTHER PUBLICATIONS

International Search Report and Written Opinion for Application No. PCT/US2017/065162, dated Mar. 29, 2018, 18 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2017/065162, dated Jun. 20, 2019, 14 pages.

Office Action for Chinese Application No. CN20178067272, dated Jul. 29, 2022, 17 pages.

\* cited by examiner

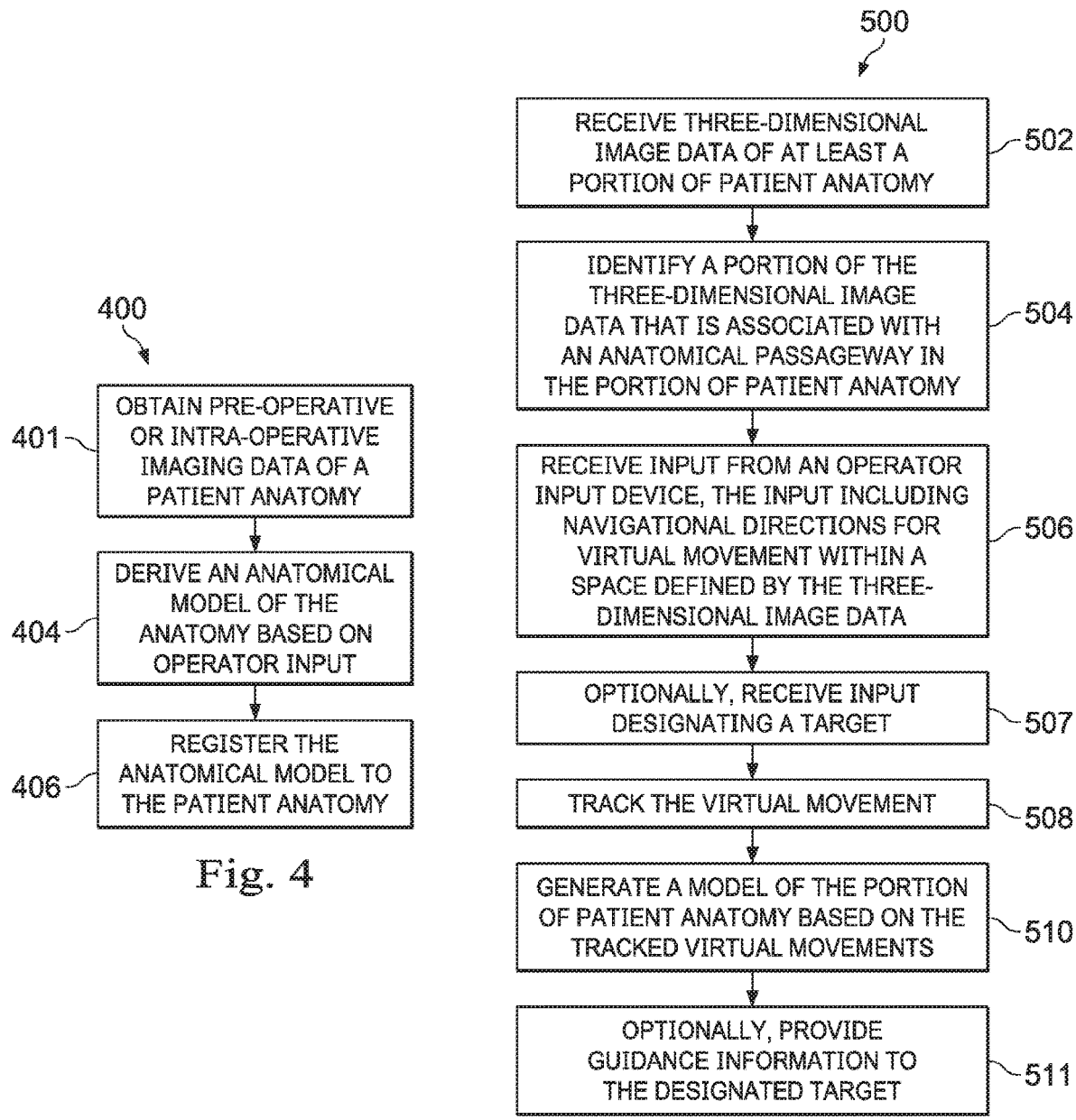

SYSTEMS AND METHODS FOR NAVIGATION IN IMAGE-GUIDED MEDICAL PROCEDURES

RELATED APPLICATIONS

This patent application is the U.S. national phase of International Application No. PCT/US2017/065162, filed Dec. 7, 2017, which designated the U.S. and claims priority to and the benefit of the filing date of U.S. Provisional Patent Application 62/431,696, entitled "Systems and Methods for Navigation in Image-Guided Medical Procedures," filed Dec. 8, 2016, which are incorporated by reference herein in their entirety.

FIELD

The present disclosure is directed to systems and methods for controlling a steerable elongate device.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device. In addition, different modes of operation may also be supported.

To facilitate such minimally invasive medical techniques, imaging registration techniques may be utilized to relate at least modality of preoperative or intraoperative imaging to the position and/or orientation of an inserted minimally invasive medical instrument to navigate and positioned the instrument with respect to the target tissue location within the patient. In this way, the operator or other operator may be able to more accurately direct and control the operation of the minimally invasive medical instruments.

Accordingly, it would be advantageous to provide improves to the use of medical imaging during minimally invasive medical techniques.

SUMMARY

The embodiments of the invention are best summarized by the claims that follow the description.

Consistent with some embodiments, a method includes receiving, by a medical imaging system having at least one processing device, three-dimensional image data of at least a portion of patient anatomy; identifying, by the processing device, a portion of the three-dimensional image data that is associated with the portion of patient anatomy; receiving, at the processing device, input from an operator input device, the input including navigational directions for virtual movement within a space defined by three-dimensional image data; tracking the virtual movement; and generating a model of the portion of patient anatomy based on the tracked virtual movements. Other embodiments include corresponding computer systems, apparatus, and computer programs recorded on one or more computer storage devices, each configured to perform the actions of the methods.

Consistent with other embodiments, a system for processing medical images is provided. The system may include a memory storing a set of three-dimensional image data of at least a portion of patient anatomy and a processing device in communication with the memory, the processing device configured to execute instructions to perform operations. The operations may include receiving three-dimensional image data of at least a portion of patient anatomy, identifying a portion of the three-dimensional image data, and receiving input from an operator input device. The input may define a pathway within an image space defined by the portion of the three-dimensional image data. The operations may further include generating a model of the portion of patient anatomy based on the pathway within the image space defined by the three-dimensional image data. Other embodiments of this aspect include corresponding computer systems, apparatus, and computer programs recorded on one or more computer storage devices, each configured to perform the actions of the methods.

Consistent with other embodiments, a system for displaying and interacting with medical images is provided. The system may include a memory storing a set of three-dimensional image data of at least a portion of patient anatomy and a processing device in communication with the memory. The processing device configured to execute instructions, stored in the memory, to perform operations. The operations may include rendering a graphical user interface in a display in communication with the processing device, receiving three-dimensional image data of at least a portion of patient anatomy, and identifying a portion of the three-dimensional image data that is associated with a portion of patient anatomy. The operations may further include receiving input from an operator input device, the input defining a pathway within an image space defined by the three-dimensional image data. The system also includes generating a model of the portion of patient anatomy based on the pathway within the image space defined by the three-dimensional image data. Other embodiments of this aspect include corresponding computer systems, apparatus, and computer programs recorded on one or more computer storage devices, each configured to perform the actions of the methods.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 4 is a flowchart illustrating a general method providing image-based guidance for an image-guided, minimally-invasive medical procedure, according to some embodiments of the present disclosure.

FIG. 5A is a flowchart of a method for generating a model or a portion of a model from three-dimensional image data without performing a segmentation process, according to some embodiments of the present disclosure.

Figure 6A:
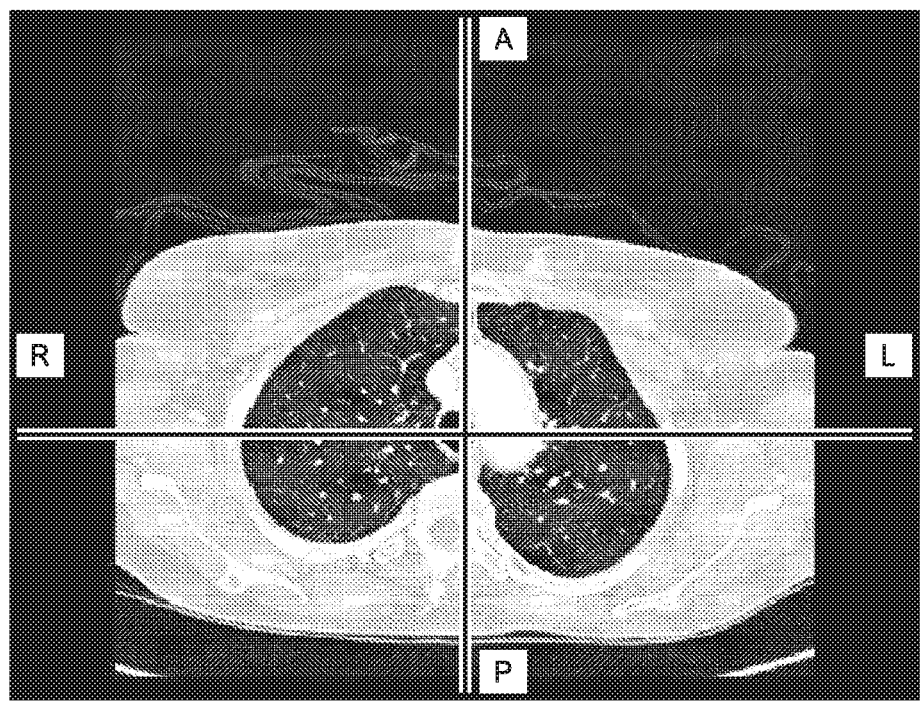
Figure 6B:
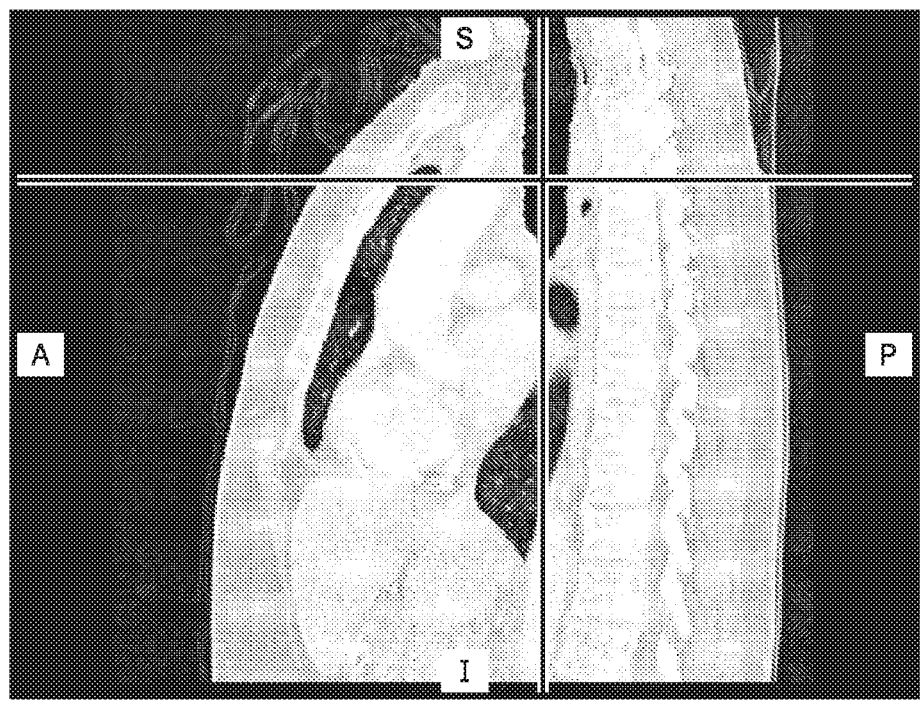
Figure 6C:
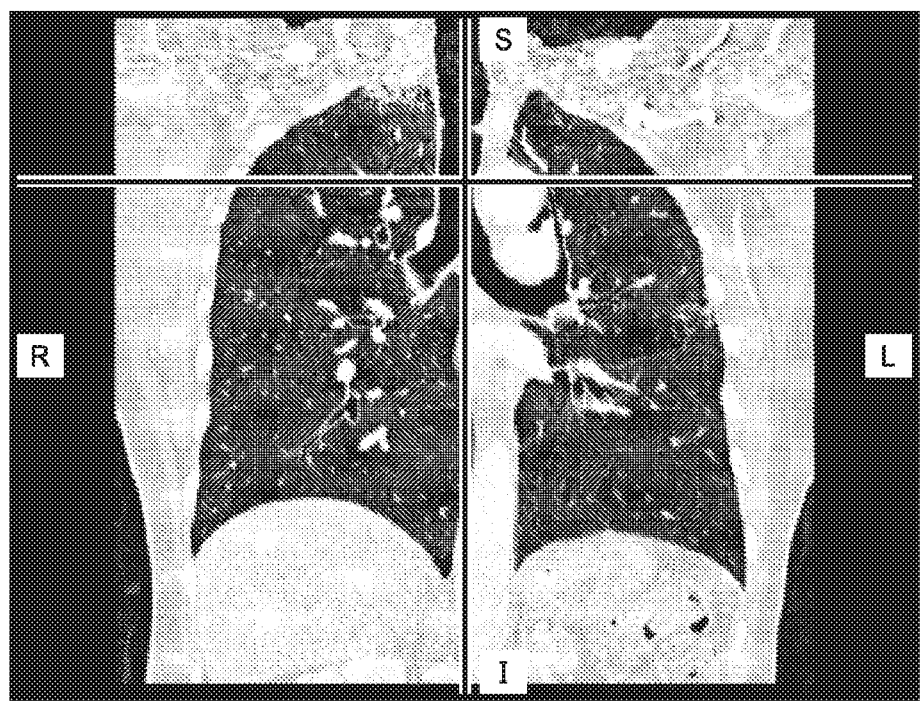

FIGS. 6A, 6B, and 6C are two-dimensional renderings of exemplary medical image data, according to some embodiments of the present disclosure.

Figure 7A:
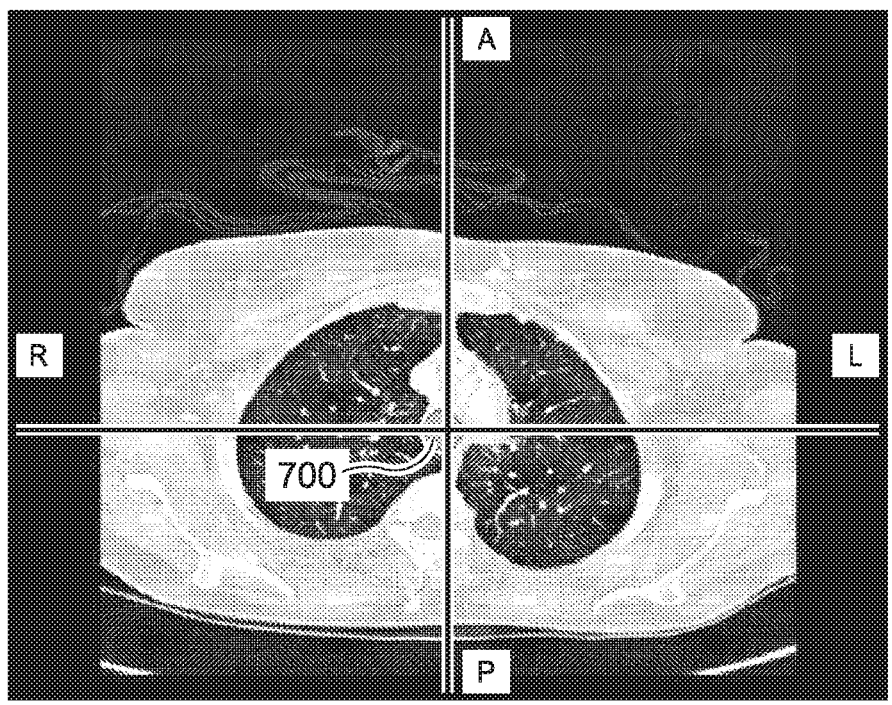
Figure 7B:
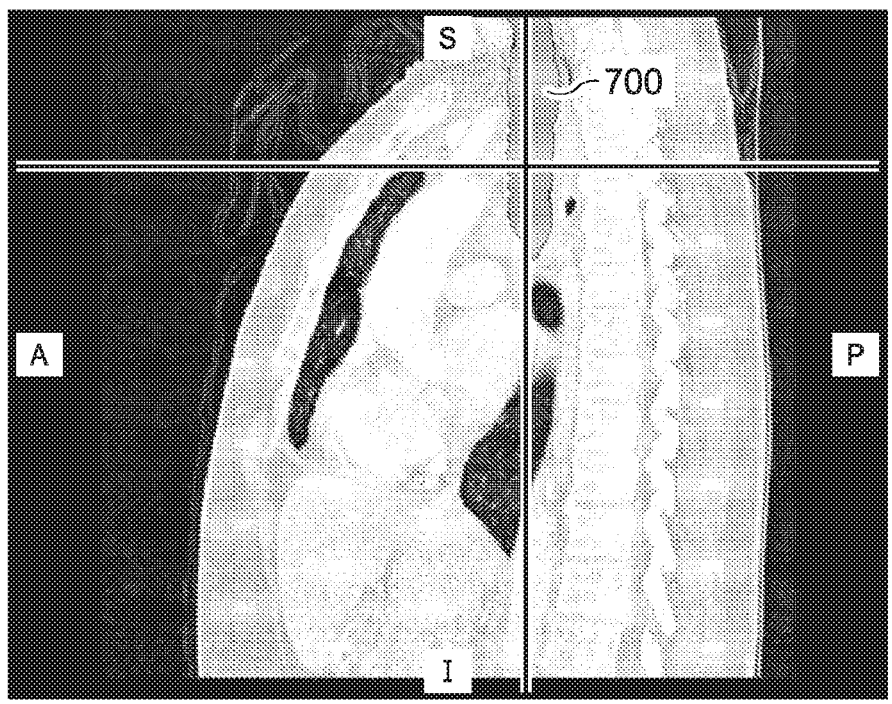
Figure 7C:
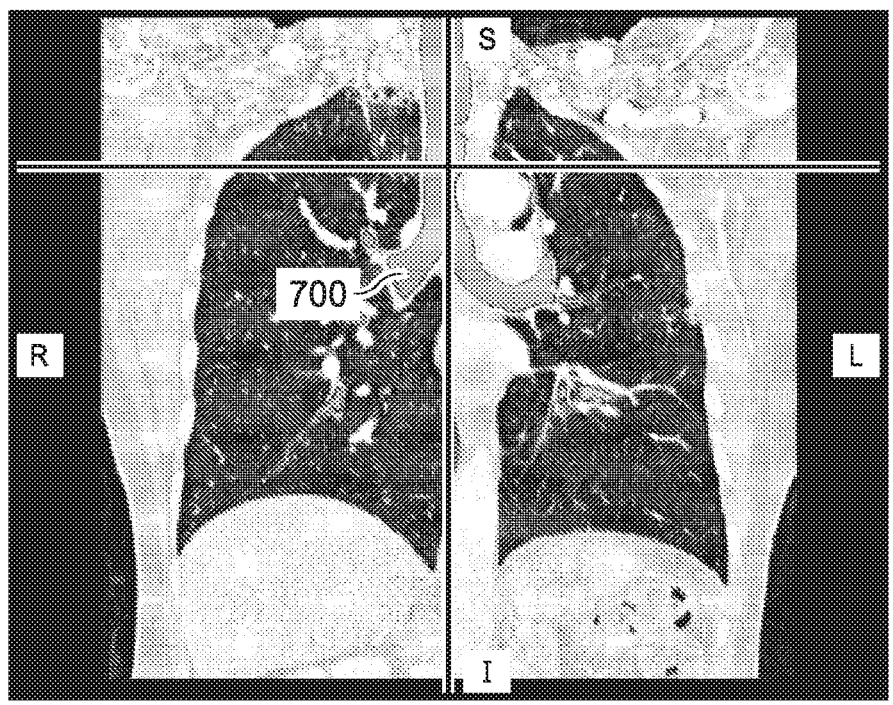

FIGS. 7A, 7B, and 7C depict multiple two-dimensional views of filtered image data, obtained by filtering the image data of FIGS. 6A-C, respectively, according to some embodiments of the present disclosure.

Figure 7D:
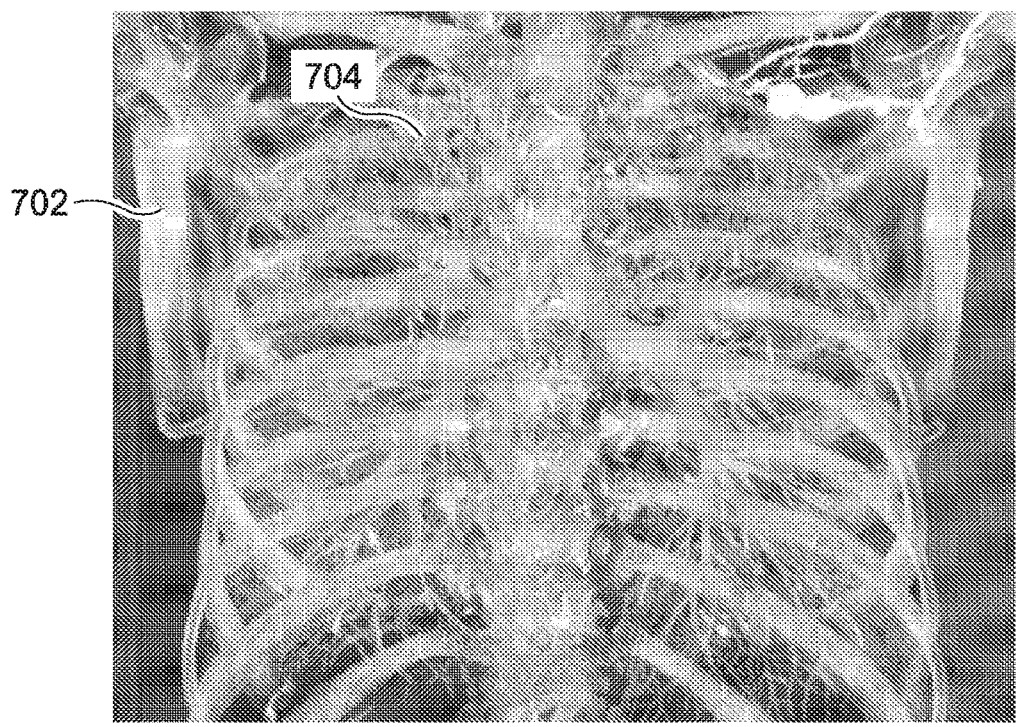
Figure 7E:
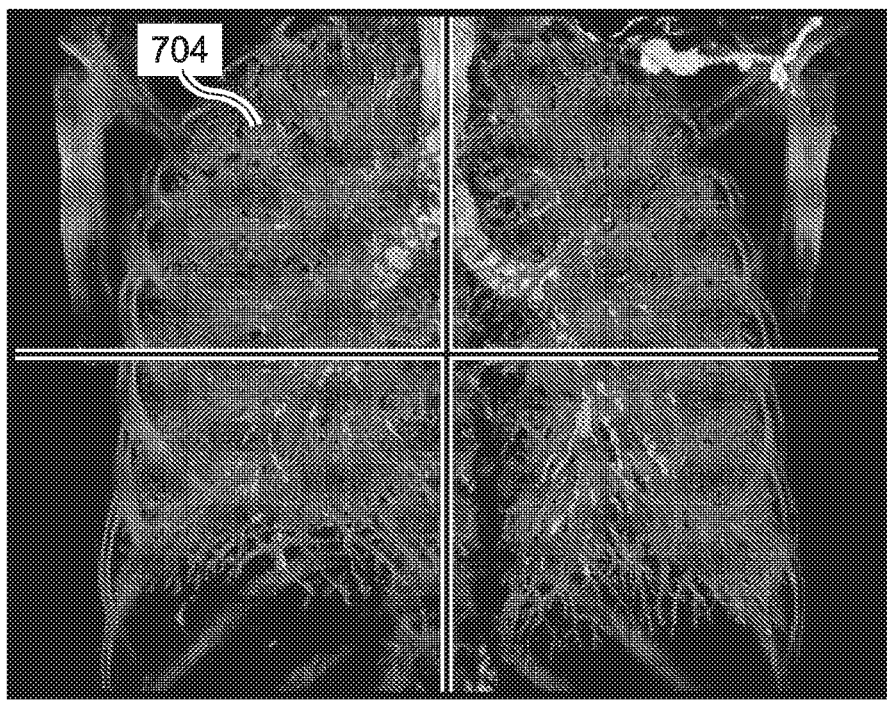
Figure 7F:
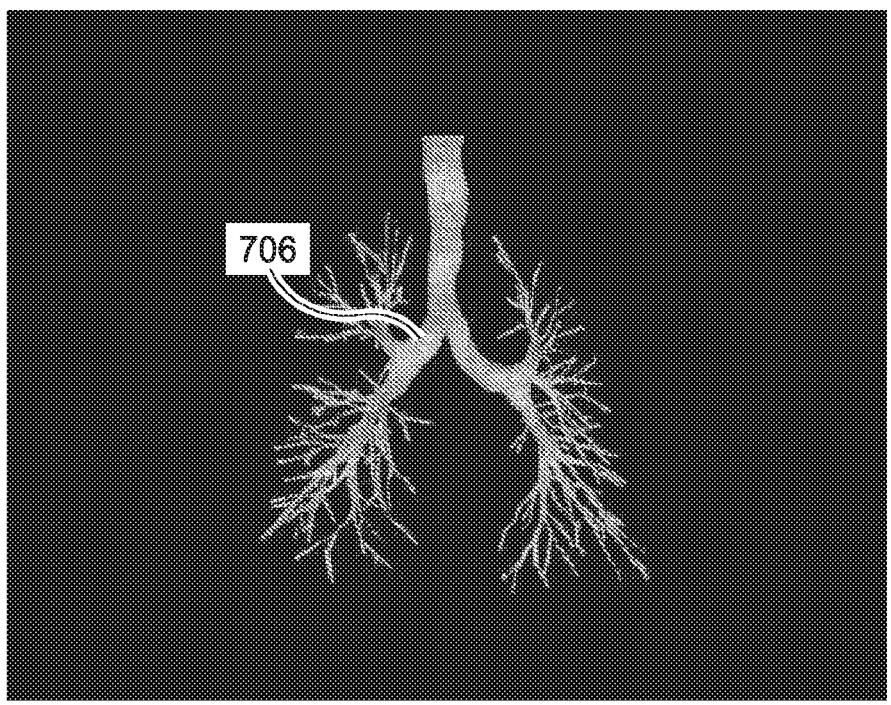

FIGS. 7D, 7E, and 7F are orthographic views of the three-dimensional filtered image data, shown in FIGS. 7A-C, according to some embodiments of the present disclosure.

Figure 8A:
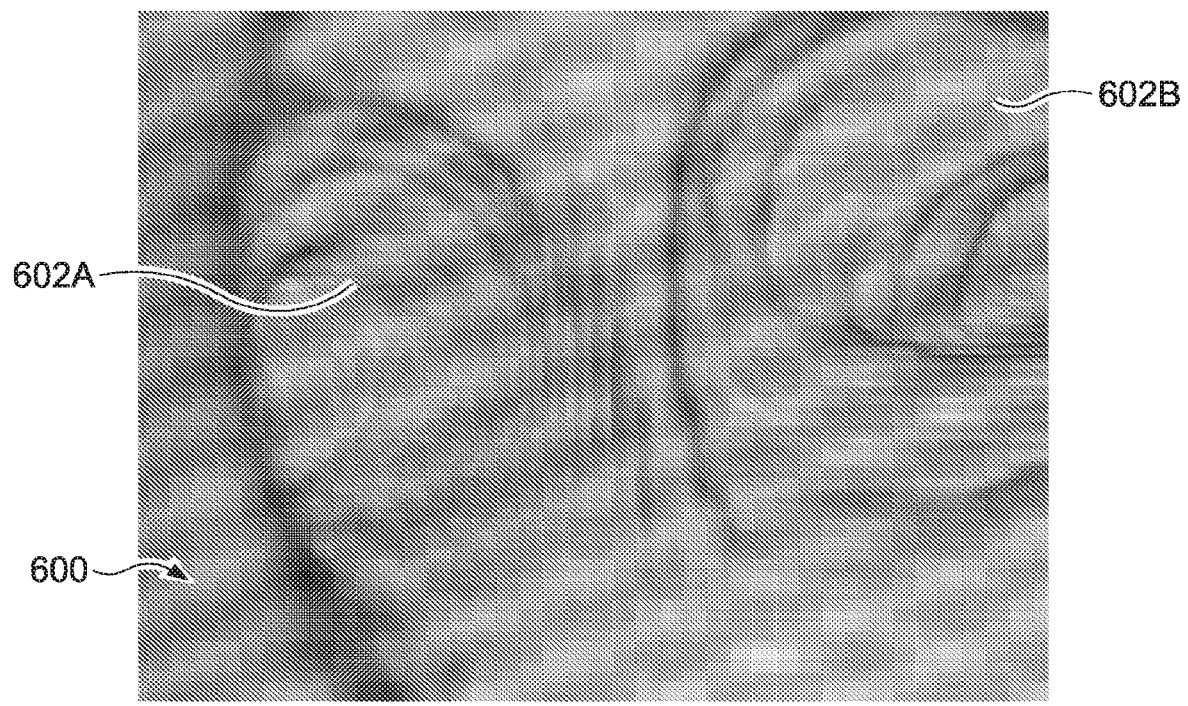

FIG. 8A is a three-dimensional rendering of exemplary medical image data, according to some embodiments of the present disclosure.

Figure 8B:
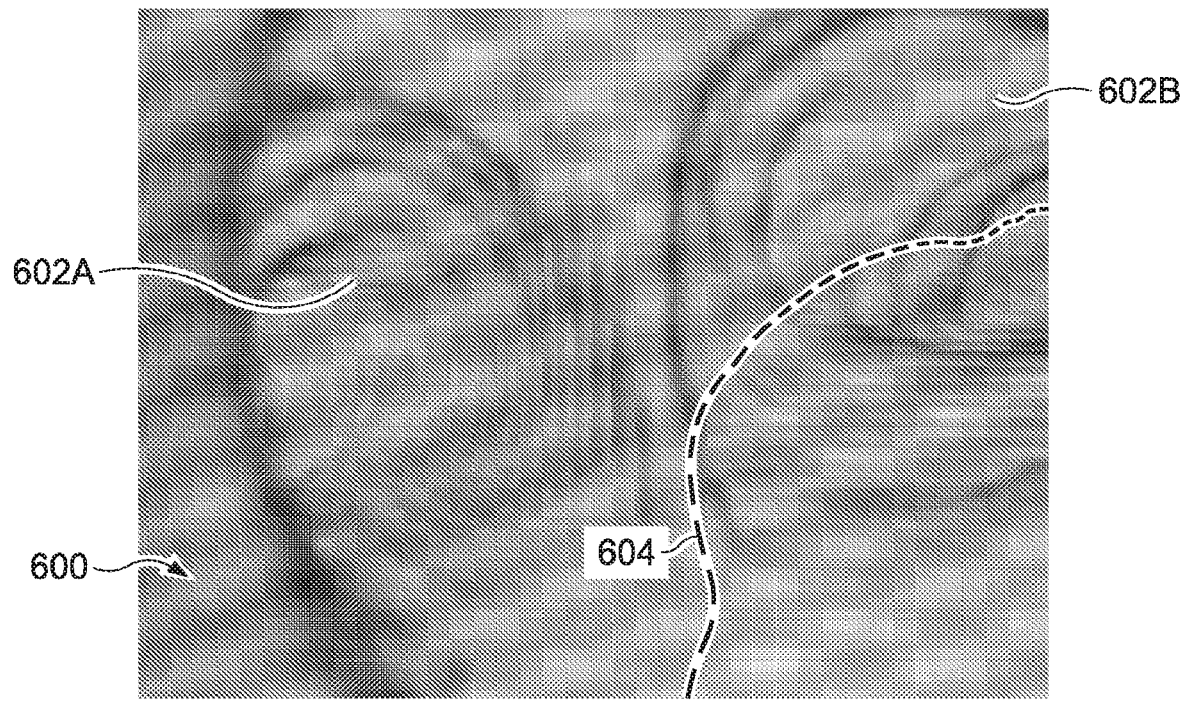

FIG. 8B is a three-dimensional rendering of the exemplary medical image data of FIG. 8A with a line-based navigational path model.

FIGS. 9A, 9B, 9C, and 9D, show exemplary image data that includes data corresponding to a target of a medical procedure, according to some embodiments of the present disclosure.

Figure 9A:
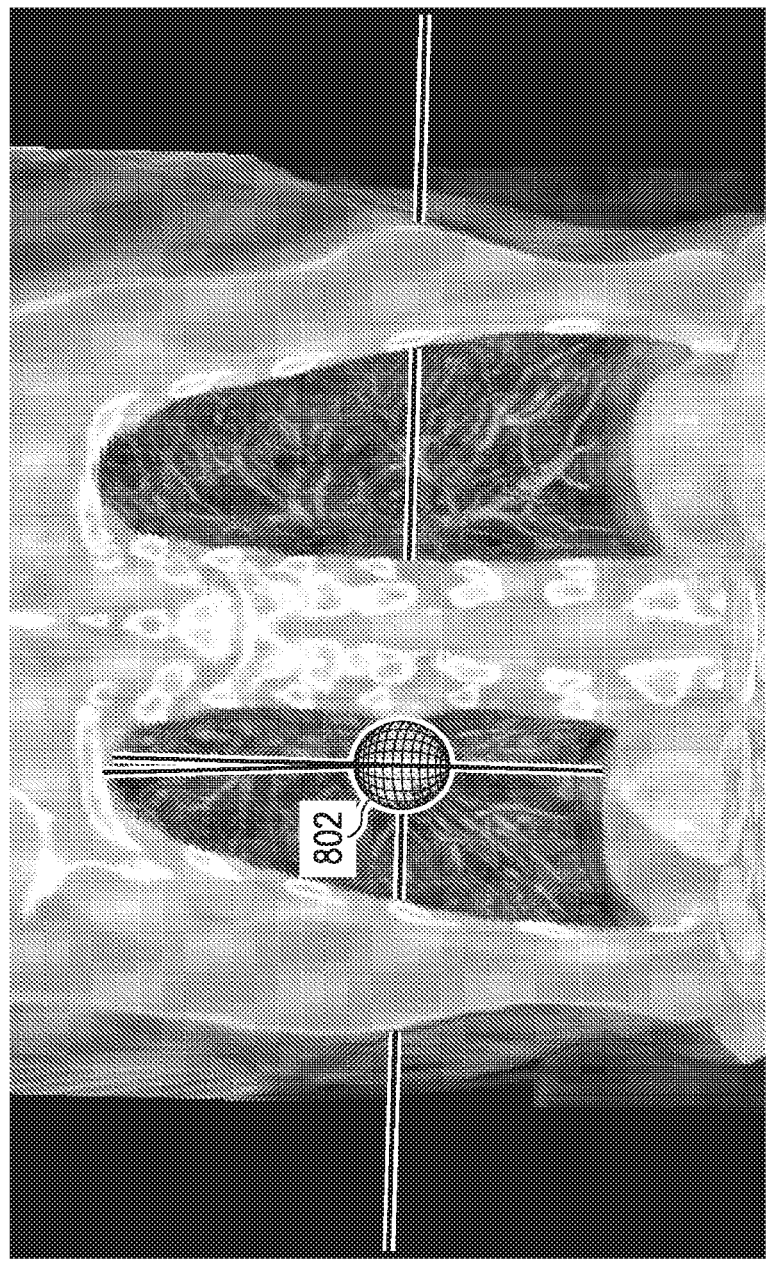
Figure 9B:
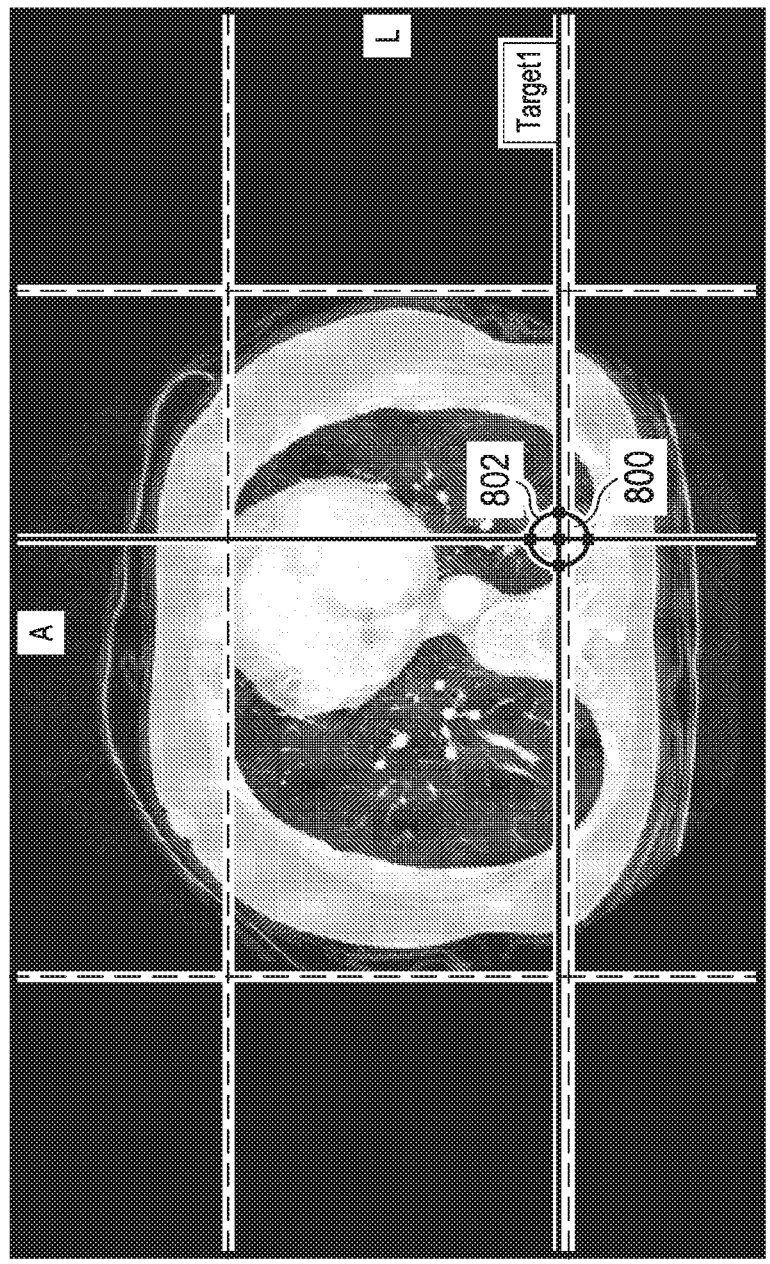
Figure 9C:
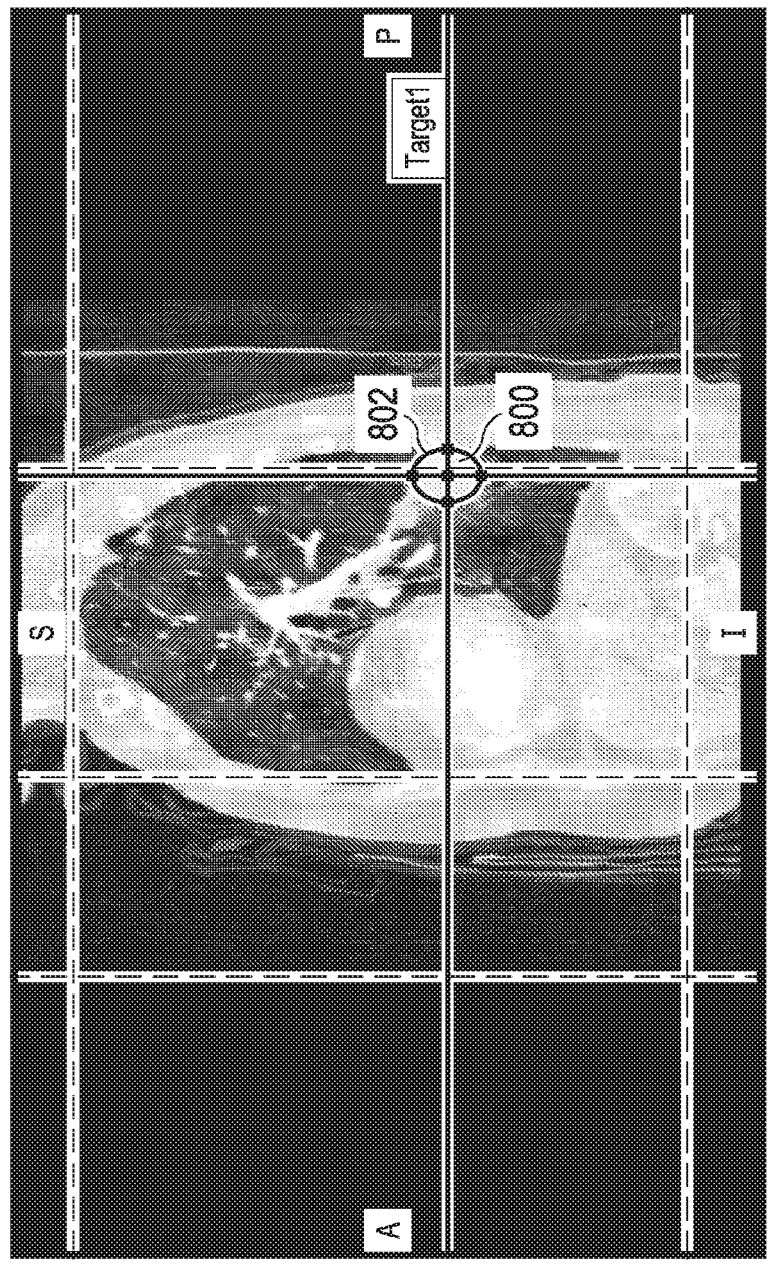
Figure 9D:
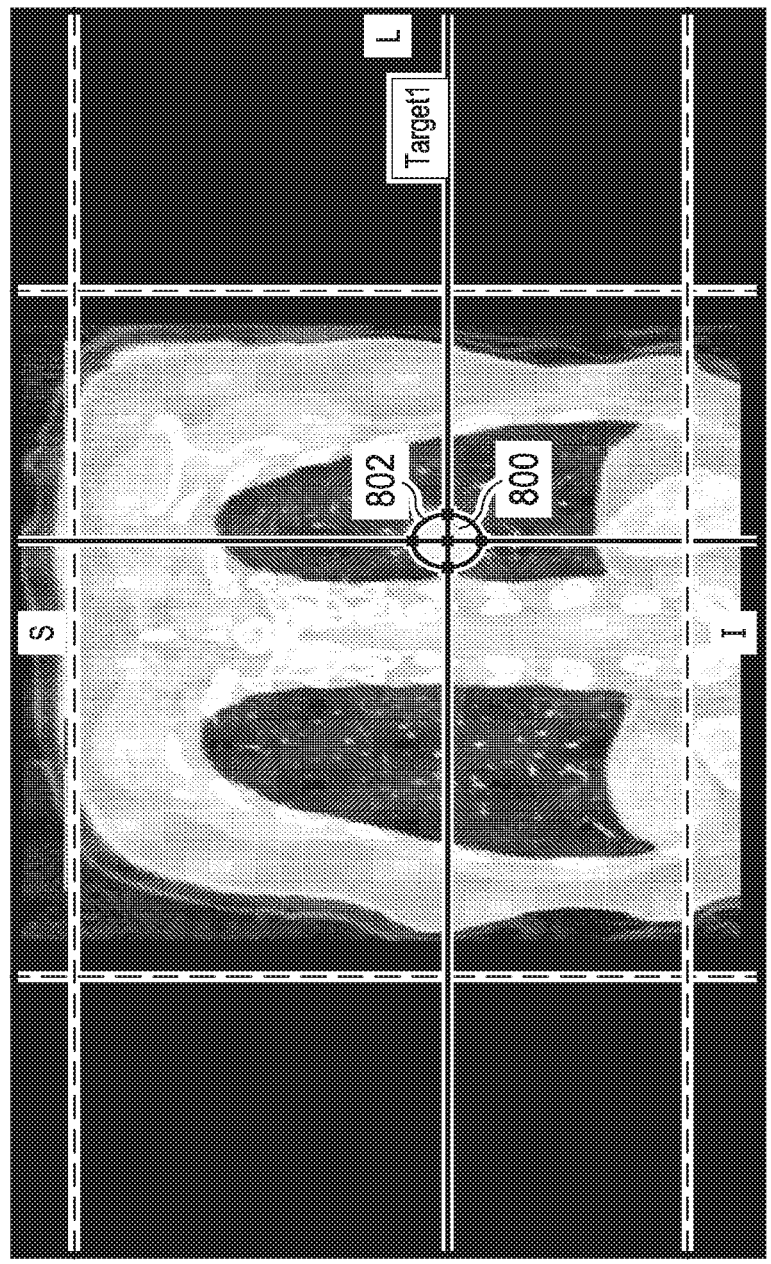
Figure 10:
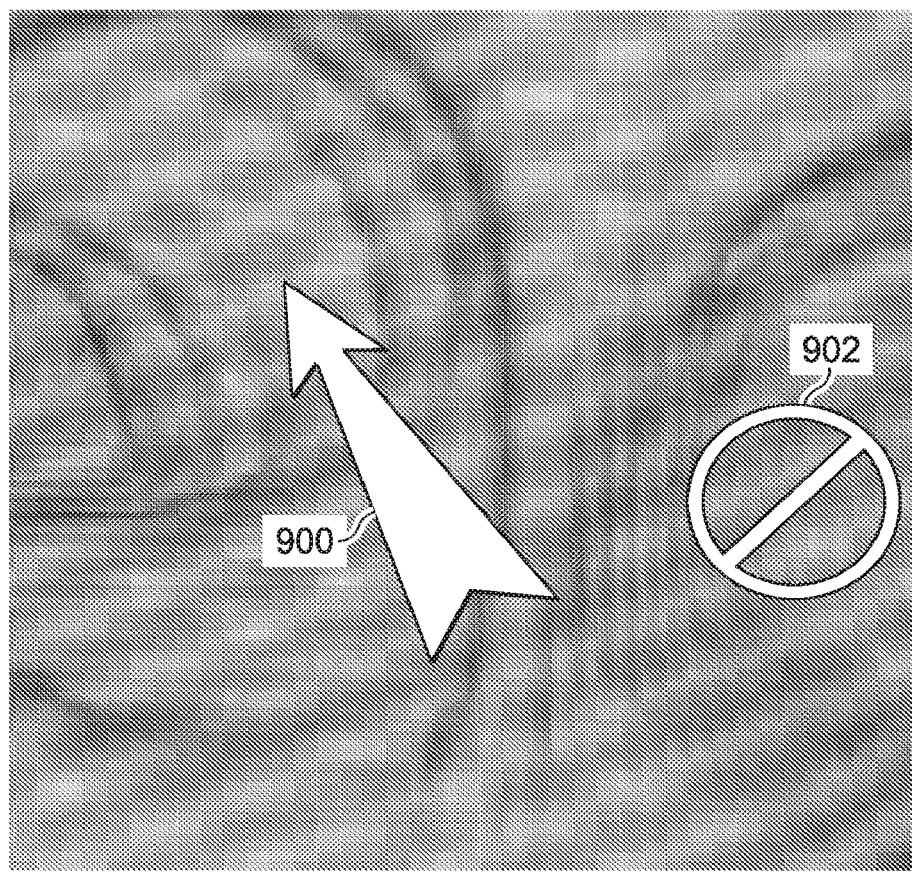

FIG. 10 shows an indicator arrow that points to the target identified in FIGS. 9A-9D from a perspective view within the three-dimensional image data, according to some embodiments of the present disclosure.

Figure 11A:
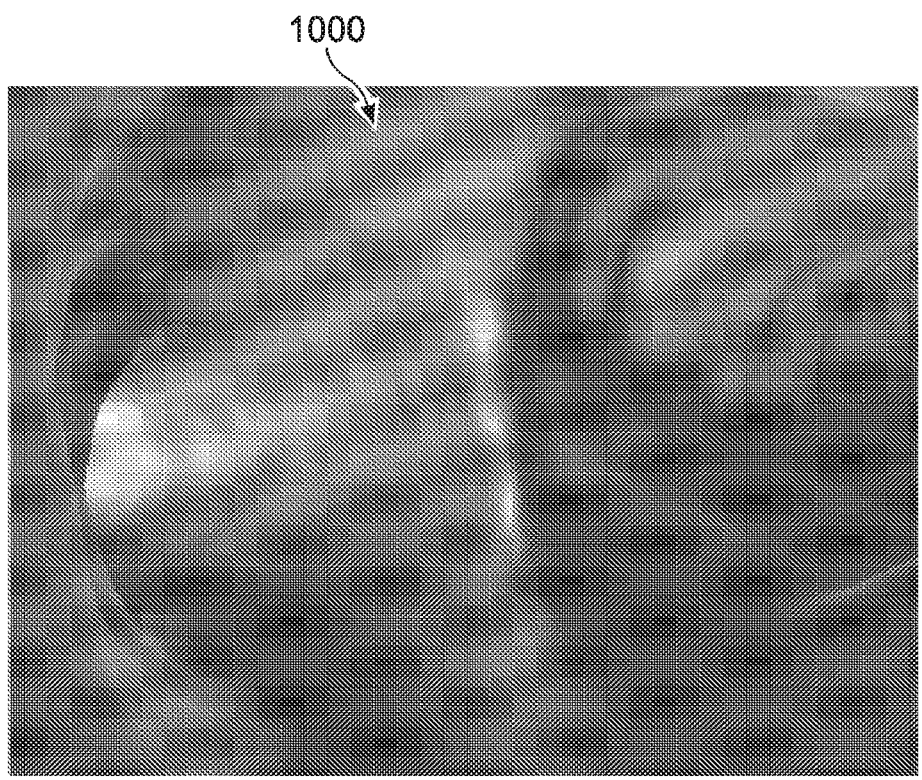

FIG. 11A shows an internal view of a surface model generated by segmenting image data, according to some embodiments of the present disclosure.

Figure 11B:
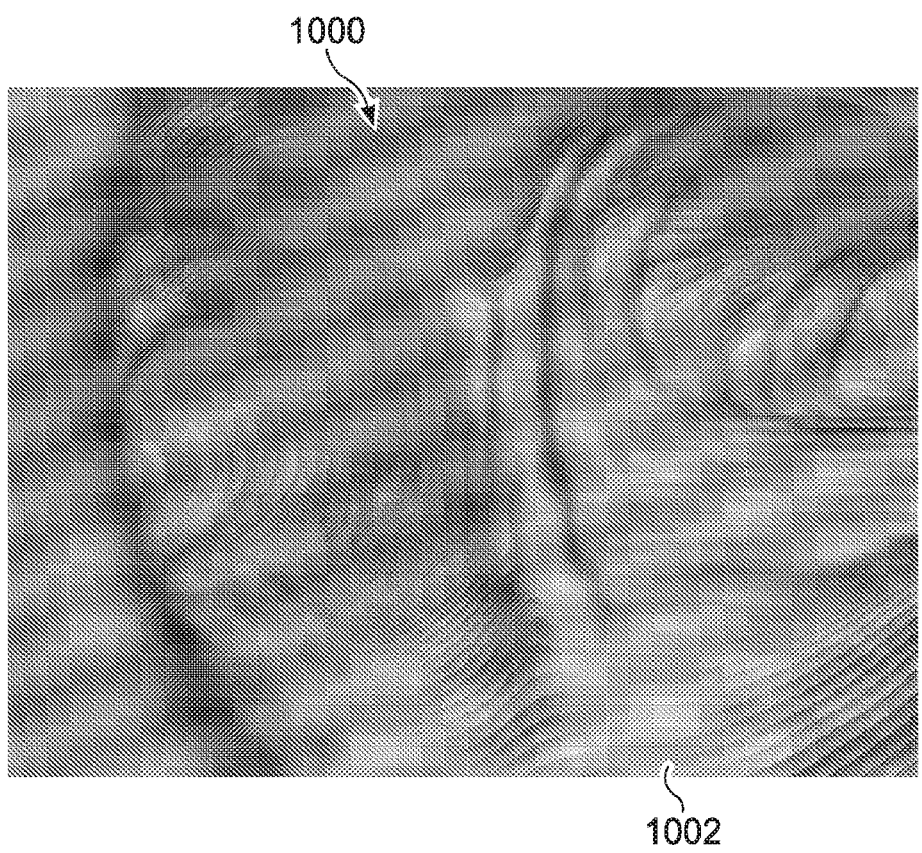

FIG. 11B shows in internal view that combines the surface model of FIG. 11A with a view of the filtered image data from which the surface model was derived, according to some embodiments of the present disclosure.

FIGS. 12A, 12B, 12C, and 12D illustrate a process of producing a model of exemplary patient anatomy, according to some embodiments of the present disclosure.

Figure 13:
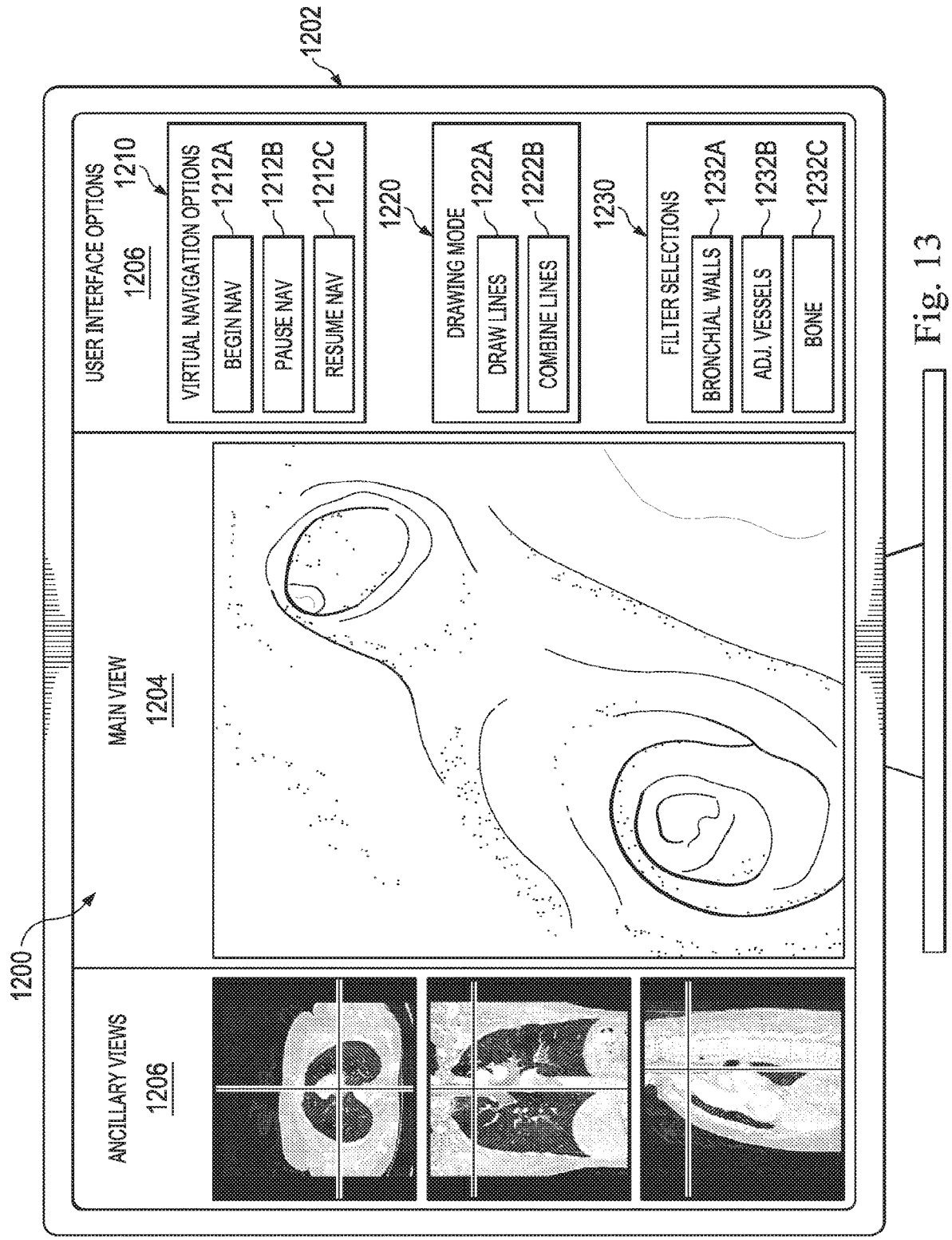

FIG. 13 is an exemplary user interface, according to some embodiments of the present disclosure.

Figure 14:
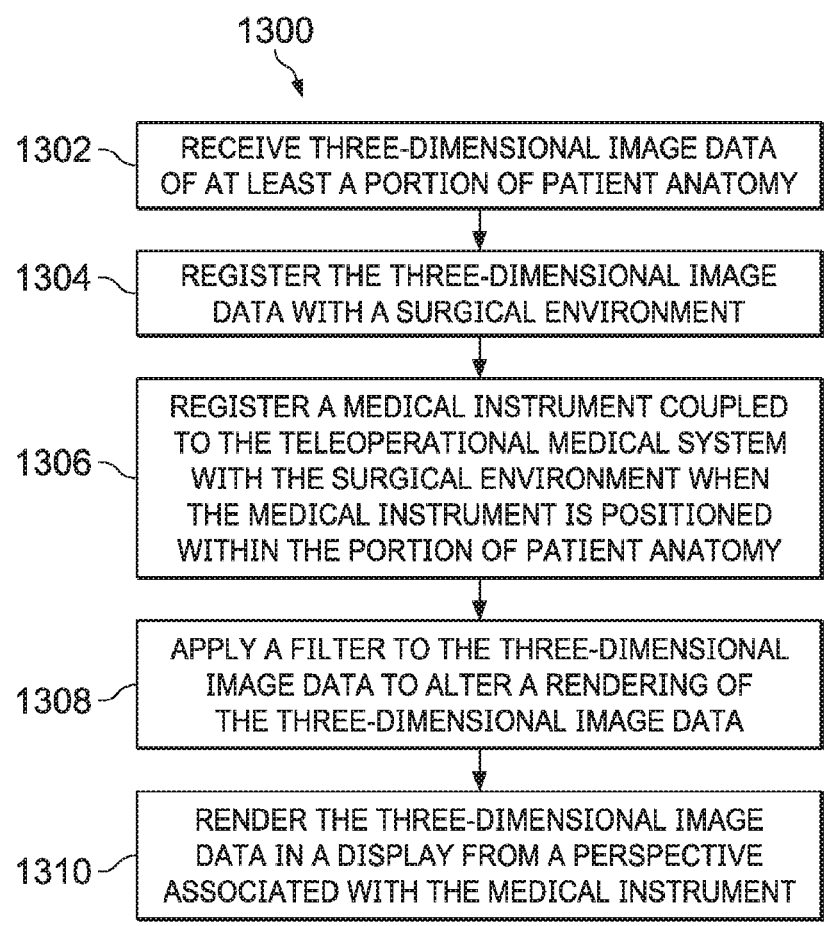

FIG. 14, shown therein is a flowchart of a method 1300 of providing image-based guidance during a minimally-invasive medical procedure, according to some embodiments of the present disclosure.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
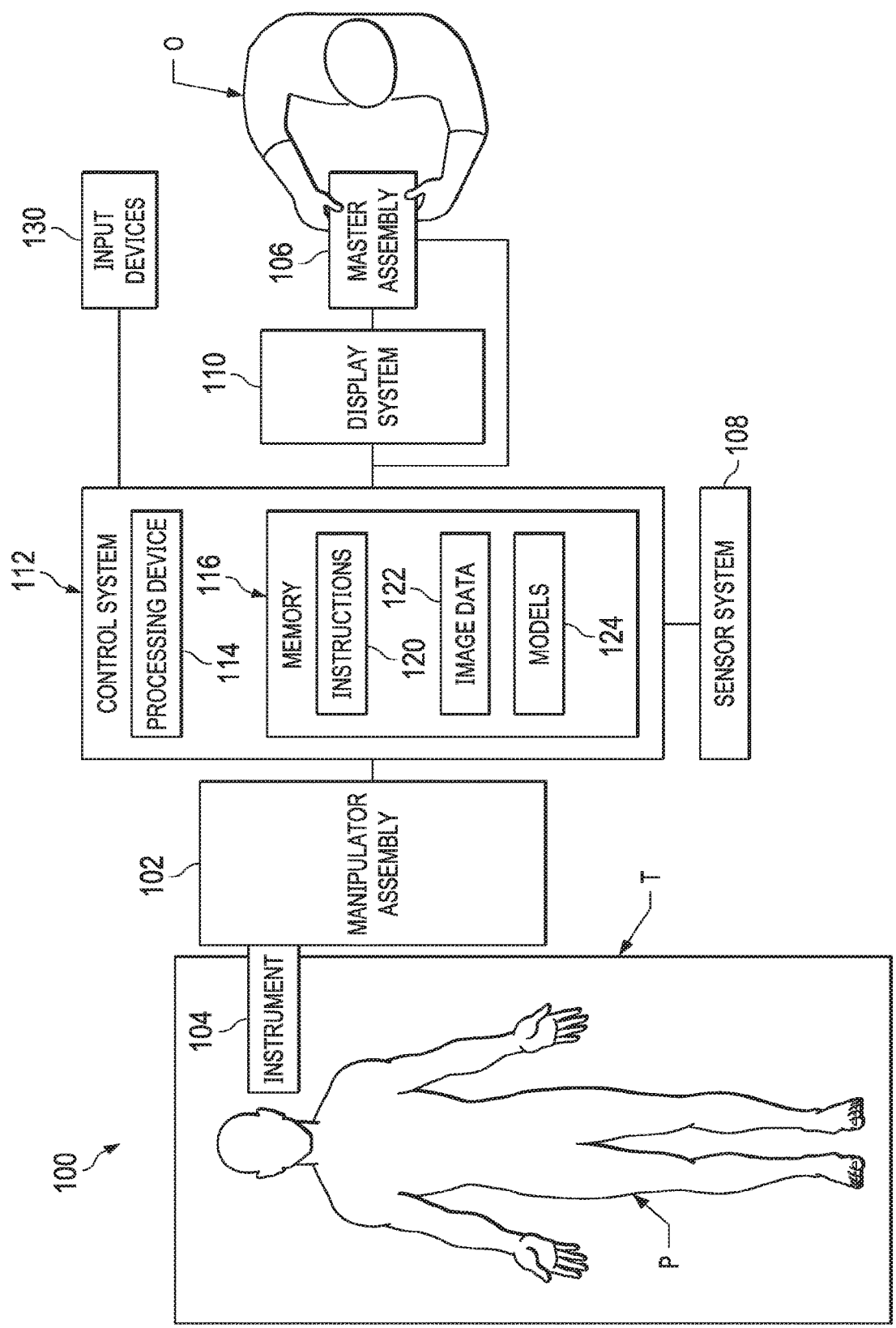
FIG. 1 is a simplified diagram of a teleoperated medical system according to some embodiments.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator O (e.g., a surgeon, a clinician, or a physician as illustrated in FIG. 1) to view the interventional site and to control teleoperational manipulator assembly 102.

Master assembly 106 may be located at an operator's console which is usually located in the same room as operating table T, such as at the side of a surgical table on which patient P is located. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. The display system 110 may also displace image data during planning and navigation operations. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processing device 114 of a control system 112, which may include a central processing unit (CPU) and a graphics processing unit (GPU).

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a operator that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O in controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory 116 and at least one processing device 114 for effecting control between medical instrument 104, master assembly 106, sensor system 108, and display system 110. Control system 112 also includes programmed instructions 120 (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processing device 114 of the control system 112 may execute instructions 120 that include instructions corresponding to processes disclosed herein and described in more detail below. Any of a wide variety of centralized or distributed data processing architectures may be employed. Similarly, the programmed instructions 120 may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

As will be describe herein in additional detail, the memory 116 may store medical image data 122, which include data obtained from a variety of medical imaging modalities, including high resolution and low resolution CT imaging systems. Additionally, as will be described in more detail herein, the memory 116 of the control system 112 may include one or more models 124. These models 124 may be derived from the image data 122 and/or from user input received via the master assembly 106 or other input mechanisms, such as the input devices 130, which may include a keyboard, a mouse, a drawing tablet, etc., whereby the operator O can virtually navigate within image data and/or draw on image data as will be described in greater detail below. For example, in some embodiments the control system 112 may be a medical workstation that provides an interface through which the operator O may plan a medical procedure. In some additional or alternative embodiments, the control system 112 may be part of a minimally invasive surgical system used in performing medical procedures.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2B:
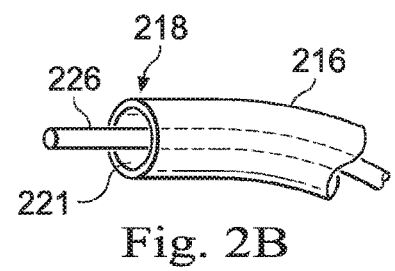
FIG. 2B is a simplified diagram of a medical instrument with an extended medical tool according to some embodiments.
Figure 2A:
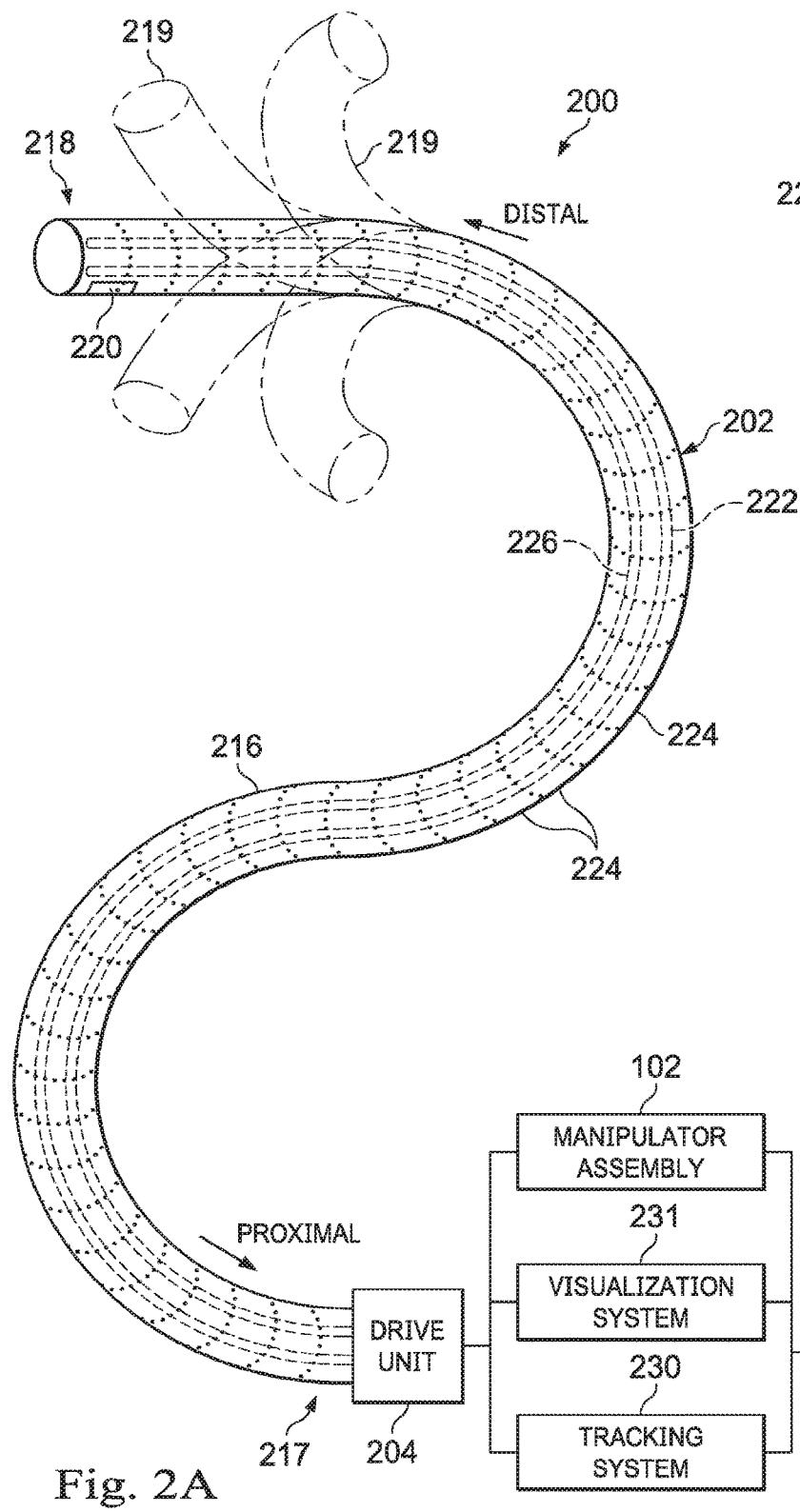
FIG. 2A is a simplified diagram of a medical instrument system according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and tip portion or distal end. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216.

In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 218. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator with real-time position information. In some examples, the real-time position information may be displayed on display system 110 of FIG. 1 for use in the control of medical instrument system 200. In some examples, control system 112 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

Figure 3A:
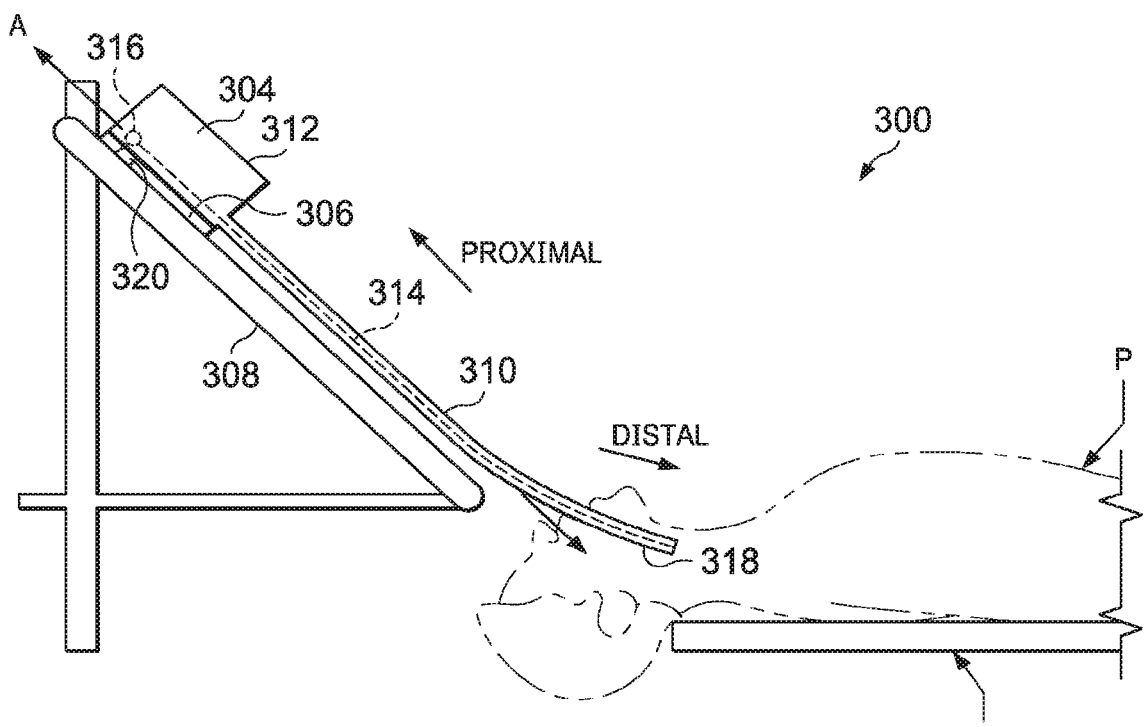
FIGS. 3A and 3B are simplified diagrams of side views of a patient coordinate space including a medical instrument mounted on an insertion assembly according to some embodiments.
Figure 3B:
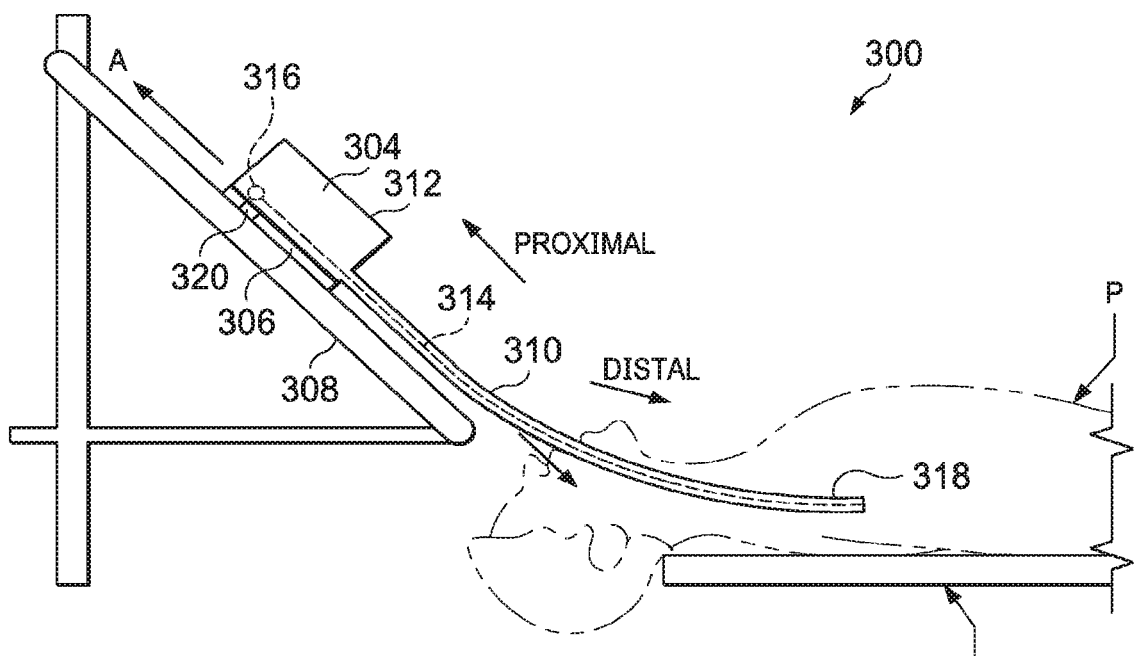

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a medical instrument 304 is coupled to an instrument carriage 306. In some embodiments, medical instrument 304 may use EM sensors, shape-sensors, and/or other sensor modalities that collect position, orientation, and/or shape information characterizing the medical instrument 304. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to medical instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Medical instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or another reference value (e.g., I=0). In FIG. 3B, instrument body 312 and instrument carriage 306 have advanced along the linear track of insertion stage 308 and distal end 318 of elongate device 310 has advanced into patient P. I FIG. 4 is a flowchart illustrating a general method 400 for enabling an image-guided minimally invasive medical procedure. The method 400 may provide for registration between medical images and an instrument, like the elongate device 202 of FIG. 2 and/or the medical instrument 304 of FIGS. 3A and 3B. The method 400 is illustrated as a series of steps or operations. Embodiments of the method 400 may include additional or alternative operations before, after, in between, or as part of the enumerated operations. In some embodiments of the present disclosure, a set of instructions may be stored on a computer readable medium, which when executed by a processor cause the machine having a processor to perform an embodiment of the method 400.

Accordingly, the method 400 may begin at operation 402, in which pre-operative or intra-operative image data is obtained from an imaging system that uses computed tomography (CT), magnetic resonance imaging (MRI), fluoroscopy, thermography, ultrasound, optical coherence tomography (OCT), thermal imaging, impedance imaging, laser imaging, nanotube X-ray imaging, or another suitable imaging modality, to provide image data. In some embodiments, the image data is stored image data obtained by retrieval from memory. The pre-operative or intra-operative image data may correspond to two-dimensional, three-dimensional, or four-dimensional (including e.g., time-based or velocity-based information) images, in various embodiments. For example, the image data may be low-resolution or lose-close three-dimensional CT data representing a portion of the patient P. The image data may represent the upper or lower torso of patient P and include data representing the heart, lungs, stomach, liver, intestines, ribs, muscles, etc. of patient P. Other embodiments may include image data from any other area of the patient P. The image data may be the image data 122 stored in memory 116 of FIG. 1.

At an operation 404, computer software alone or in combination with manual input is used to convert the recorded images into a two-dimensional or three-dimensional composite representation or model of a partial or an entire anatomic organ or anatomic region. Some methods for generating a model from image data may include a segmentation process that identifies certain features of a model, such as the curvature of a bronchial passageway in the lung, extracts the curvature, and uses that to generate a centerline model representing the bronchial passageway. This segmentation relies on artificial intelligence to generate the model, such as the centerline model. However, segmentation can fail when the image quality is insufficient or for other reasons. Because image quality can be crucial to segmentation, higher doses of imaging agents and/or radiation may be used and/or required to provide image data of a sufficient quality for automated segmentation. Thus as described herein, the conversion of the imaging data into a model may be done without segmenting the image data and instead of applying a segmentation process, input from the operator O may be received and used to generate a model at the operation 404. For example, the input may include navigational directions for virtual movement within a space defined by the image data received from one or more of the input devices 130. The navigational directions may be used in place of or as a centerline model, similar to a centerline model which could be derived from a segmentation process.

At an operation 406, the model derived from the operator input may be used to register the image data to the patient P while the patient P is on the operating table T as shown in FIG. 1 and in FIGS. 3A and 3B. By registering the derived model and the associated image data to the patient P, the image data may be used for navigation and positioning of a minimally invasive instrument within the patient P to perform an image-guided procedure. Generally, registration involves the matching of measured point to points derived from the model through the use of rigid and/or non-rigid transforms. Measured points may be generated by driving the minimally invasive instrument to landmarks in the anatomy, and tracking position of the instrument using electromagnetic coils scanned and tracked during the procedure, or a shape sensor system. The measured points may be generated for use in an iterative closest point (ICP) or another point set registration methods may also be used in registration processes within the scope of this disclosure. Some appropriate examples of point cloud registration techniques may be found in U.S. Provisional Patent Application No. 62/205,440, filed Aug. 14, 2015, entitled "SYSTEMS AND METHODS OF REGISTRATION FOR IMAGE-GUIDED SURGERY," and in PCT/US16/046633, filed Aug. 11, 2016, entitled "SYSTEMS AND METHODS OF REGISTRATION FOR IMAGE-GUIDED SURGERY," the disclosures of which are incorporated herein, in its entirety, by reference. Other registration techniques may be used in other embodiments.

FIG. 5A is a flowchart of a method 500 for generating a model or a portion of a model from three-dimensional image data without performing a segmentation process. Some embodiments of the method 500 may be understood as embodiments of the operation 404 of FIG. 4. The method 500 is depicted as a series of enumerated operations. Embodiments of the method 500 may include additional or alternative operations before, after, in between, or as part of the method 500 as shown in FIG. 5A. Some embodiments of the method 500 may omit one or more of the enumerated operations. Additionally, some embodiments of the method 500 include a set of instructions stored on a computer readable medium, like the instructions 120 stored in memory 116 of FIG. 1. The processing device may execute the set of instructions to cause a medical system, like system 100 of FIG. 1 or a component thereof, to perform the operations of the method 500.

As illustrated, the method 500 may begin at operation 502 in which a medical system having at least one processing device receives three-dimensional image data of at least a portion of patient anatomy. For example, the processing device 114 of the control system 112 may receive the image data. The three-dimensional image data may be CT data, including low-dose CT data, or other image data derived from a different imaging modality. The image data may represent imaged tissue and anatomical structures as a set of voxels positioned within a three-dimensional image space or image reference frame. Each of the voxels may include a density value, such as a radiodensity value, or another value that can be used to distinguish between different types of tissue, fluids, structures, etc., within the image space. For example, when the image data is CT image data, a Hounsfield value measured in Hounsfield units may be associated with each voxel. Other radiodensity values may be utilized in other embodiments. FIGS. 6A-6C illustrate exemplary medical image data that may be used to at operation 502.

At operation 504, the processing device may identify a portion of the three-dimensional image data that is associated with one or more anatomical passageways in the imaged portion of patient anatomy. FIGS. 7A-7F illustrate two and three-dimensional views of filtered image data, obtained by filtering the image data. As part of identifying the portion of the three-dimensional image data, the processing device may filter the image data according to the Hounsfield value of each voxel. For example, the processing device may filter the image data using a lower Hounsfield value threshold and/or an upper Hounsfield value threshold to identify specific features within the image space. In some examples, the density of anatomical structures or tissue may differ depending on structure or tissue type, correlating to high or low Hounsfield values. For example, because the density of air within the anatomical passageways of the lungs is so low, a correspondingly low Hounsfield value filter may be applied to the image data to effectively isolate the air in the anatomical passageways of the lungs. In this way, the processing device may identify, within the image data, the boundaries of the anatomical passageways within the lungs.

Additionally, one or more threshold values may be applied adaptively, such that different areas of the three-dimensional image data are subjected to different thresholds. For example, in order to identify structures within the image data, a first threshold value may be applied that identifies major airways within the image data. This first threshold value may be applied during a first pass of the data. Thereafter, a second pass of a data filter may be applied. The second pass may include a second threshold value that better identifies smaller branches in the airways included in the three-dimensional image data. In this and other ways, an adaptive airway threshold may be used to identify the anatomical passageways in the image data. In some embodiments, the second threshold value may be applied based on the terminal voxels identified in the first pass. In other embodiments, duplicate data sets including the three-dimensional image data may be subjected to different thresholds and then combined together. Such a process may resolve some amount of noise occurring in the image data.

In other embodiments, the processing device may filter the image data to identify the tissues that form actual walls of the bronchial passageways of the lungs or the blood vessels that lie just outside the bronchial walls of the lungs. In some embodiments, user input may be received in a request to display specific types of tissue, or as a request to adapt a Hounsfield value filter with a specific setting or specific adjustment. Some other types of tissues or materials that may be identified and selectively displayed include: bones, muscles, blood vessels, bronchial walls, the pleura, tumors, lesions, and fluids, such as blood. As noted herein, organs other than the lungs may be analyzed using the features and processed described herein, such that other tissues and materials may be displayed. The filtered image data may be presented to the operator O in a display, such as the display system 110, and the operator O may interact with the control system 112 to adjusting one or more filters applied to the data.

At operation 506, after displaying the filtered image data in the display, the processing device may receive input from an operator input device, such as one of the input devices 130 of FIG. 1. The input may define navigational directions for virtual movement within the image space of the filtered image data. FIG. 8A illustrates the image space of the filtered image data that the operator may view while navigating and providing the input to the operator input device. In this example, the operator O may manipulate the filtered image data such that a perspective of the image data is centered upon the upper opening of the trachea, which the operator O may visually identify in the image data. Once the perspective is set, the operator O may use the input devices 130 to move within the filtered image data with the display being updated to show the new perspective of the filtered image data after each input is received. For example, the operator O may use a keyboard having arrow keys, a mouse, a scroll wheel, a trackball, a three-dimensional input device, and/or any other suitable input device to navigate within the filtered image data.

Optionally, at operation 507, the processing device may receive input from the operator input device designating a portion of the image data as a target (e.g. target 800 in FIG. 9B-D).

At operation 508, the processing device may track the input as virtual movement within the image space. For example, the processing device may generate a list or history of received commands relative to the image space, such that a pathway defined by the input received from one or more of the input devices 130 may be generated by the processing device 114. As the operator O moves within the image space and the processing device tracks the virtual movements, the virtual movements may provide information for a model of the anatomical passageways being virtually navigated. The tracked pathway may be used to generate a model of the navigated portion of the patient anatomy, at operation 510. For example, the tracked pathway may form a linear model having one or more lines in three-dimensional space. By maintaining the perspective within the anatomical passageways while virtually navigating through the displayed anatomical passageways, the operator O may generate these lines within the three-dimensional image space. The lines or pathways may then define a model similar to a centerline model which would result from a segmentation process. However, the navigational pathways are obtained without using segmentation of the image data. The operator O may interact with the input devices 130 to indicate whether the navigational pathways are approximately centered within the anatomical passageways or are disposed close to the bottom or top edge of the anatomical passageways. FIG. 8B illustrates a line-based navigational path model 604. One or more models may be produced from the navigational pathways using a diameter associated with the navigated passageway.

Optionally, at operation 511, the processing device may provide guidance information to help guide the operator) to the designated target (e.g. target 800 in FIG. 9B-D).

Figure 5B:
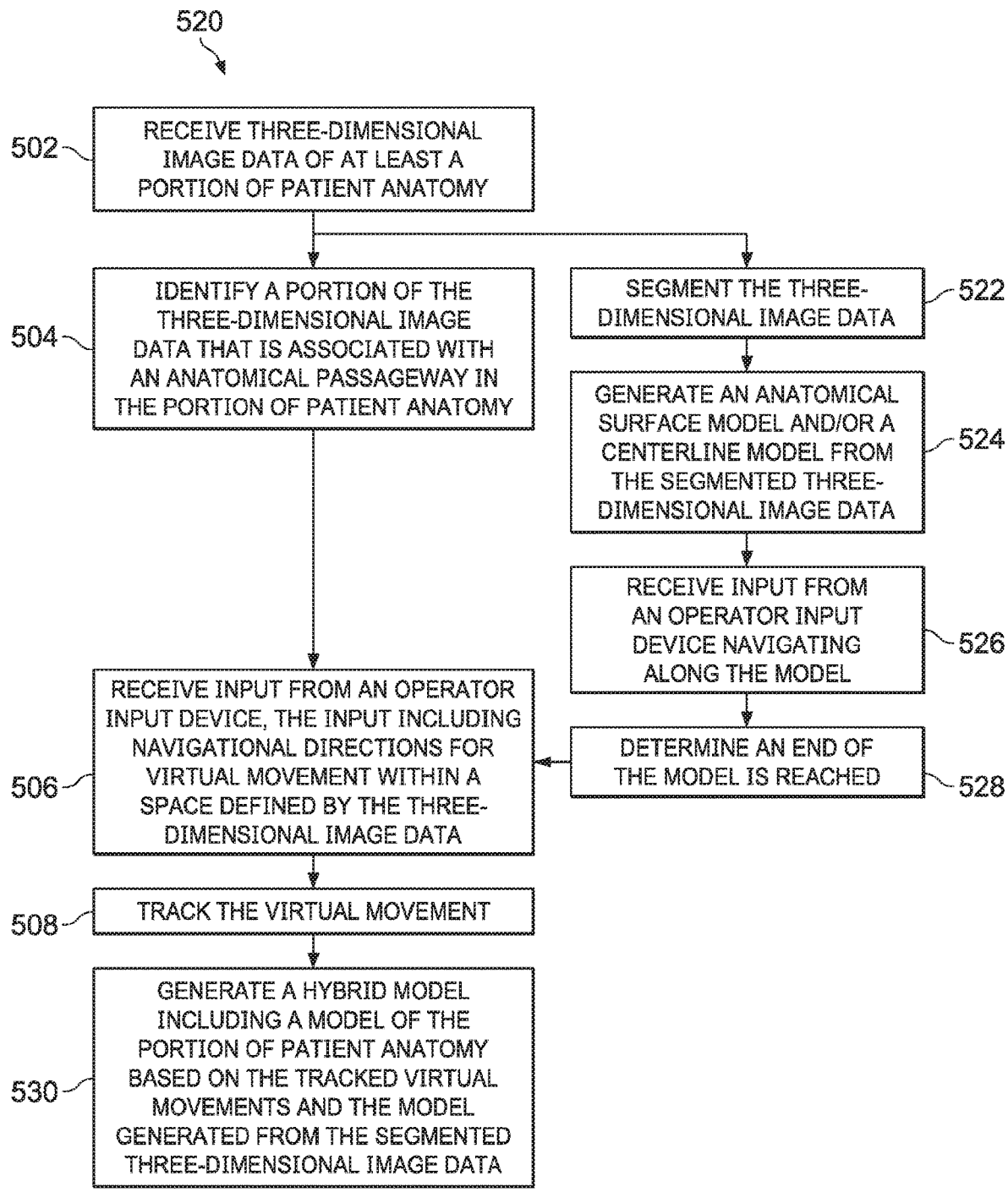
FIG. 5B is a flow chart of a method for generating a model or a portion of a model from three-dimensional image data using a segmentation process for a portion of the model generation, according to some embodiments of the present disclosure.

In some embodiments, the input provided by the operator O may generate an entire model, which may be used subsequently in a registration process. In another embodiment, as described in FIG. 5B, a hybrid technique uses available segmentation information to supplement the method 500. FIG. 5B is a flowchart of a method 520 for generating a hybrid model or a portion of a model from three-dimensional image data with some portions of the model generated with a segmentation process and some portions of the model generated without performing a segmentation process. Some embodiments of the method 520 may be understood as embodiments of the operation 404 of FIG. 4. The method 520 is depicted as a series of enumerated operations. Embodiments of the method 520 may include additional or alternative operations before, after, in between, or as part of the method 520 as shown in FIG. 5B. Some embodiments of the method 520 may omit one or more of the enumerated operations. Additionally, some embodiments of the method 520 include a set of instructions stored on a computer readable medium, like the instructions 120 stored in memory 116 of FIG. 1. The processing device may execute the set of instructions to cause a medical system, like system 100 of FIG. 1 or a component thereof, to perform the operations of the method 500.

As illustrated, the method 520 may begin at the operation 502, as previously described for method 500. At an operation 522, a segmentation algorithm may be used to segment the three dimensional image data. Segmentation identifies certain features of a model, such as the curvature of a bronchial passageway in the lung to extract the curvature. At an operation 524, the features extracted from the segmentation process are used to generate a centerline model and/or surface model (e.g., a mesh model) representing the bronchial passageway. For example, a segmentation algorithm may be used to generate a centerline model defining the trachea and the primary bronchii of the lungs. The centerline model may be displayed along with the CT image data in the display system 110. At an operation 526, optionally, the processing device may receive input from an operator input device navigating through or along the model generated by segmentation. For example, the operator O may navigate along the centerline model until the distal end of the centerline model portion is reached. At an operation 528, a termination point for the model generated by segmentation is identified and may serve as a starting point for generating a model based on user input. Thus, the segmentation algorithm may be used to generate a centerline model of a portion of the patient anatomy then the input provided by the operator O may be used to, continue the model, enhance the model, or add missing portions of the patient anatomy to the model.

After the end of the segmentation model is reached, the method may continue to the operation 506, as previously described, in which the processing device may receive input from an operator input device, such as one of the input devices 130 of FIG. 1. The input may define navigational directions for virtual movement within the image space of the filtered image data. Optionally, the processing device may detect the end of the centerline model and may automatically begin tracking navigational movements of the operator O as the operator navigates beyond the centerline model within the filtered image data. As noted, segmentation may fail when image quality degrades below a threshold. For example, low-dose CT image data may provide adequate information to a segmentation algorithm for larger passageways within the lungs, but may fail as the passageways narrow and as the number or resolution of voxels defining more distal passageways decreases. However, the operator O may be able to determine the approximate boundaries of these distal passageways visually in the filtered image data shown in the display system 110. The operator O may virtually navigate (i.e., navigate within the image space) through the image data to define pathways that may be used to augment the segmented model where the segmentation has failed. At the operation 508, the processing device may track the input as virtual movement within the image space. Thus, the tracked navigational movement of the virtual driving by the operator beyond the trachea and the primary bronchii of the lungs, in this example, may provide for input data that can be used to expand the centerline model to secondary and further generations in the lung, providing for a more complete model of the patient anatomy. A hybrid model is generated by the segmented data and the tracked pathway may, at operation 510. For example, hybrid models may include at least one centerline derived from segmentation and at least one navigational pathway derived from virtual navigation inputs received from the operator. Accordingly, one exemplary model may include a proximal centerline model portion derived from segmentation having a distal end connected to a navigational pathway model portion, which in turn has a distal end connected to a distal centerline model portion derived from segmentation.

In some situations, unique aspects of a portion of an anatomical passageway may cause failure of segmentation at that particular portion. For example, a lesion, tumor, blockage, or wound may be present at that portion of the anatomical passageway and distort the anatomical passageways in a way that cannot be resolved or is difficult to resolve by the segmentation algorithm. In some embodiments, the operator O may virtually navigate through the particular portion that was not segmented. The operator O may then request through the input devices 130 that operation of a segmentation algorithm may be resumed based upon a distal end of the pathway defined by the virtual navigation. Because the problem that caused the failed segmentation may not be present distally from the particular portion, the segmentation algorithm may be able to continue after the operator O has navigated beyond the particular problematic portion.

Referring now to FIGS. 6A, 6B, and 6C, shown therein are renderings of exemplary medical image data that may be used in a method (e.g. method 500, 520) for generating a model without performing a segmentation process. FIG. 6A presents an anterior view of the chest region of patient P taken in an axial plane; FIG. 6B is a lateral view of the chest region taken in a coronal plane, and FIG. 6C is a frontal view of the chest region taken in a sagittal plane. The views shown in FIGS. 6A-C are cross-sectional views obtained from three-dimensional data. These views are "slices" showing two-dimensional planes within the three-dimensional image data. The air in the lungs in FIGS. 6A-C is depicted in black.

Referring now to FIGS. 7A, 7B, and 7C, these figures depict multiple on-axis views of filtered image data, obtained by filtering the image data of FIGS. 6A-C. FIGS. 7A-C highlight voxels 700 that have a Hounsfield value that may be associated with the air in the anatomical passageways of the lungs. The air within the lungs of patient P may be the least dense portions of the patient P and may be filtered by density value to isolate the anatomical passageways. FIGS. 7A-C are cross-sectional slices that depict the voxels having the density of air within the trachea and other passageways in the lungs of the patient P. These voxels may be identified by filtering according to the Hounsfield value and rendered differently than other voxels so as to highlight the anatomic passageways to the operator O. In some embodiments, the image data may be filtered to show the air in the anatomical passageways of the lungs as a distinctive color so as to provide a model of the passageways.

FIGS. 7D, 7E, and 7F are orthographic views of the image data, shown in FIGS. 7A-C, being further filtered so as to highlight or depict specific aspects of the patient anatomy included in the image data. FIG. 7D is filtered based on Hounsfield values to depict portions of bone 702 the vasculature 704 surrounds the bronchial walls 706 of the lungs of patient P. Through a user interface, the operator O may select specific tissues from a menu of selectable tissues for rendering in the user interface and vasculature 704. Based on the selections, FIG. 7E may be presented to the position. FIG. 7E shows the vasculature 704 and the bronchial walls 706. The operator O may also interact with the user interface to select only the bronchial walls 706 for display as seen in FIG. 7F. The use of active, selective filtering of the imaging data based on a characteristic of each voxel other than its location may provide the operator O with a desired rendering. Additionally, by filtering the image data, the computing resources (CPU and/or GPU resources) required to render the data and update the view of the data as the operator O virtually navigates through the data to generate a model as part of a planning process. As described below in connections with the user interface 1200 of FIG. 13, the operator O may interact with user interface elements to selectively apply and modify filters to the image data.

FIG. 8A depicts the three-dimensional image data of FIGS. 6A-6C and 7A-7D from a particular perspective relative to an anatomic passageway within the image data. More specifically, FIG. 8A illustrates a three-dimensional rendering of anatomic passageways from a driving perspective, for example from the perspective of a device, such as an endoscope, being navigated through the anatomic passageways. The air in the lungs in FIG. 8A is rendered transparently, so that the operator O may view the interior of the bronchial passageways. By making the air within the lungs transparent, the three-dimensional view of FIG. 8A provides the operator with a navigable perspective of the CT image data. As shown in FIG. 8A, the image data is filtered to render the air transparent while rendering the voxels having Hounsfield values of the lung walls 600. In this way, the interior surface of the lung walls 600 is presented to the operator O to enable the operator O to virtually navigate within the walls 600. The perspective shown in FIG. 8A is indicated by vertical and horizontal guidelines shown in FIGS. 6A-C and 7A-C, which intersect at the perspective point of FIG. 8A, and is directed toward the main carina of the lungs of the patient P. As seen in FIG. 8A, looking distally from the trachea, there is the left bronchus 602A and the right bronchus 602B.

FIG. 8B is a three-dimensional rendering of the exemplary medical image data of FIG. 8A with a line-based navigational path model. FIG. 8B illustrates a navigational pathway 604 which has been generated from performing a method such as method 500, previously described. The navigational pathway 604 may be generated by tracking the virtual movements of the operator O within the image space. As shown in FIG. 8B, the operator O has already navigated down the right bronchus 602B, forming the navigational pathway 604, and has returned to the trachea. The operator O may then navigate down the left bronchus 602A, further performing processes 506, 508, and 510 of method 500, which will generate another navigational pathway, like the navigational pathway 604. This other navigational pathway may be connected to the navigational pathway 604 and combined into a single line-based model of the lungs of the patient P. The line-based model is generated based on the navigational inputs received from the operator O as the operator O virtually navigates within the image space.

Referring now to FIGS. 9A, 9B, 9C, and 9D, shown therein is image data, similar to that shown in FIGS. 6A-C and FIGS. 7A-F, such as CT image data that includes data corresponding to a target 800 of a medical procedure. For example, the target 800 may be a tumor such as a lung tumor. In some implementations, filtering the CT data by density may facilitate identification of the location and shape of the tumor. In some embodiments of the method 500, the processing device 114 may identify the target 800 or make a preliminary identification of the target 800. This may be done using the Hounsfield values associated with the voxels of image data and/or based on a comparison of stored CT data of patient anatomy that does not include the target or that includes a target of a different size. For example, identification of the target 800 may be facilitated by comparison of image data collected at different times. Some embodiments, for example as described in the optional processes 507, 511 of the method 500, an input may be received via a user interface from the operator O designating a portion of the image data as the target 800. For example, the operator O may provide input on a display screen 110 displaying each of the two-dimensional slices of FIGS. 8B-8D. The inputs received on each of the three views may be used to produce a target identification zone being centered around a position in the three-dimensional image space shown in three-dimensional perspective in FIG. 8A. The target identification zone may further include a three-dimensional shape formed around the central position. For example, the three-dimensional shape 802 may include as shown in FIG. 8A, an oval, a cube, etc. The operator O may interact with a UI element to control the size and shape of the three-dimensional shape 802. After the position and shape of the three-dimensional shape 802 have been received, the three-dimensional shape 802 may be used as the target 800 or the processing device may identify the voxels within the shape 802 that make up the target 800.

FIG. 10 shows a portion of the image data obtained at operation 502 of method 500 of FIG. 5A. After the target 800 has been identified within the image data, the processing device may determine a vector between a current perspective within the image data and the three-dimensional position of the target 800. As shown in FIG. 10, the current perspective can be from the trachea at the carina of the lung. In this example, the target 800 is identified to be located within a particular lobe, e.g. the left lobe, such that the vector provides a directional indication of the location of the target. The vector may be rendered in a user interface as an arrow 900 or another user interface element representing the vector to show the operator O the location of the target 800 relative to the navigational position within the three-dimensional data. Alternatively, portions of the image data could be displayed as a different color, shade, texture or transparency indicating the target location.

In some embodiments, after the target 800 has been identified within the image data, the processing device may determine that some modeled passageways do not provide access to the target. For example, the processing device may determine that certain passageways do not have a point within a pre-determined threshold distance from the target 800. As another example, the processing device may determine a subset of the modeled passageways that does have at least one point within a threshold distance from the target 800. The threshold distance may be in a range from about 0.5 to about 5 cm. In some embodiments, the threshold distance may be in a range from about 1.5 to about 3 cm. After the processing device determines which modeled passageways can provide access to the target 800, the processing device may prevent navigation down any of the passageways that do not provide access to the target 800. As shown in FIG. 10, a marker 902 may be rendered along with the image data to communicate to the operator that the passageway shown at the right of the image in FIG. 10 does not provide access to the target 800. While in some embodiments, the processing device may display the marker 902 without preventing operator navigation down the corresponding model passageway, other embodiments may display the marker 902 and prevent navigation beyond a three-dimensional location associated with the marker 902.

Referring now to FIGS. 11A and 11B, some embodiments of the method 500 may additionally include a step of segmenting the image data to produce a surface model from the image data received in process 502 and/or produce a centerline model associated with the surface model or the image data. As shown in FIG. 11A, an internal perspective view of a surface model 1000 may be rendered in the display system 110 of FIG. 1. The surface model 1000 may be obtained by any appropriate segmentation process. However, as noted above, segmentation can fail providing for a partially segmented surface model. Thus, as shown in FIG. 11B, the physician O may request that both the surface model 1000 and the filtered image data 1002 be displayed simultaneously in the display system 110. Additionally, the operator O may interact with a user interface element to select between display of the surface model 1000 and display the filtered image data 1002. The view of information provided to the operator in FIG. 11B may permit the operator to visualize any differences between the surface model 1000 and the associated filtered image data 1002. The operator O may then continue with processes 504 through 510 to supplement the partially segmented surface model and produce a more complete segmented surface model.

Additionally, in some embodiments of the method 500, a segmentation process may be used initially to generate a first surface model with an associated centerline model. However, because the segmentation process may fail at some distance away from a target, such as the target 800 of FIGS. 9A-D, the operator O may then provide input to produce a model that extends further into the patient anatomy so that a complete model is available for utilization in an image guided medical procedure. In other words, inputs received from the operator O may be used to augment a segmented model.

Figure 12A:
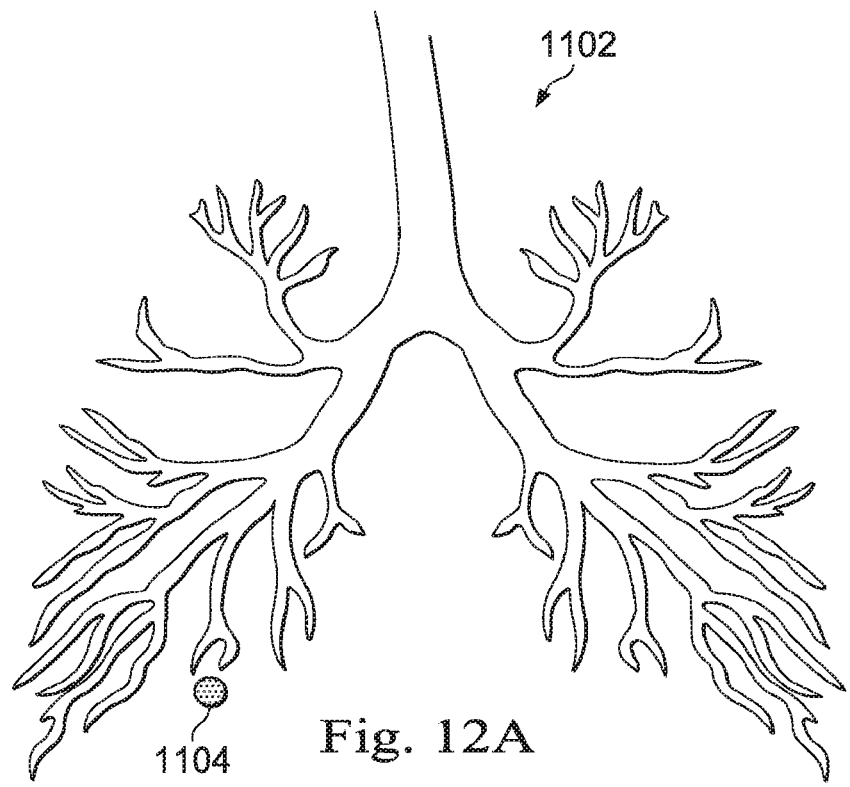
Figure 12B:
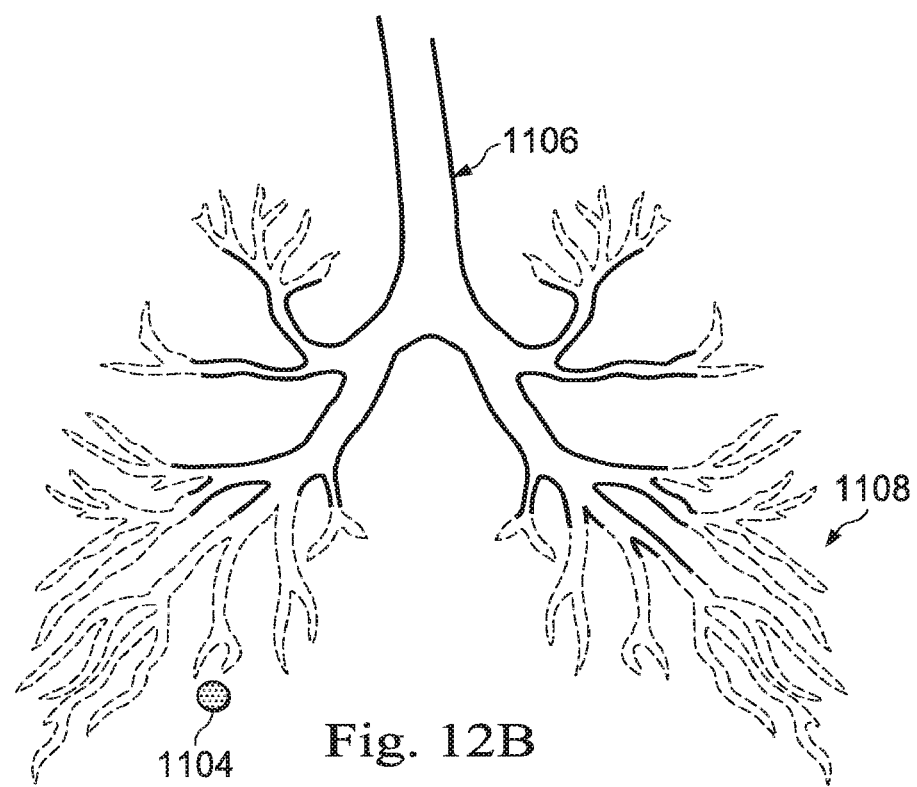

Thus FIGS. 12A, 12B, 12C, and 12D illustrate some of the steps of some embodiments of the method 500 illustrated in FIG. 5A which provide for augmentation of an initial segmented model which failed at a distance from the target. FIG. 12A illustrates a set of filtered image data 1102 that includes a set of anatomic passageways created from pre-operative or intra-operative imaging data. In this embodiment, the passageways are airways of a human lung, although method 500 is not limited to any particular anatomic structures. The filtered image data 1102 is depicted as two-dimensional for ease of explanation. As such, the depicted image data 1102 may be understood as a two-dimensional representation of the three-dimensional bronchial walls 706 of FIG. 7F. The set of filtered image data 1102 may further include image data corresponding to a target 1104, such as the target 800 as described herein with respect to FIGS. 9A-D. Because of the quality of the image data 1102 or due to anomalies in the structure of the anatomic passageways, a segmentation process performed from the processing device 114 of FIG. 1 may not be able to generate a surface model and/or a centerline model that extends through the anatomic passageways from the trachea to the target 1104 as shown in FIG. 11A. For example, FIG. 12B depicts the result of a segmentation process which may be used in some embodiments of the method 500 of FIG. 5A. FIG. 12B shows the outline of an exemplary surface model 1106 shown in solid lines. FIG. 12B also shows unsegmented portions 1108 of the anatomic passageways that were not segmented by the segmentation process by the dashed lines. Because the target 1104 can only be accessed via the unsegmented portions 1108 of the anatomic passageways, the performance of a minimally invasive medical procedure at the site of the target 1104 may be impossible or difficult using only the surface model 1106.

Figure 12C:
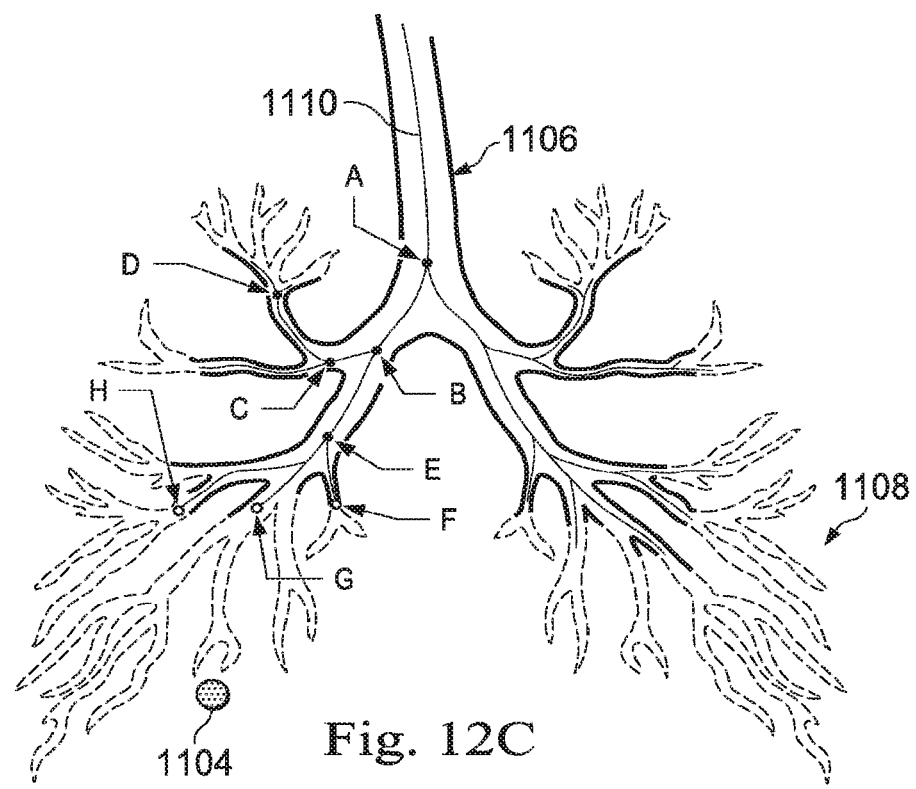

After an initial segmentation process that generates a surface model 1106, a centerline segmented model 1110 may be generated as shown in FIG. 12C. The centerline segmented model 1110 may include a set of curved and/or straight lines that extend in three-dimensional space and that correspond to the approximate center of the passageways contained in the segmented model 1106. The higher the resolution of the model, the more accurately the set of straight or curved lines in the model 1110 will correspond to the center of the passageways. Representing the lungs with the centerline segmented model 1110 may provide a smaller set of data that is more efficiently processed by one or more processors or processing cores than the data set of the segmented model 1106, which represents the walls of the passageways. In this way the functioning of the control system 112 may be improved. As shown in FIG. 12C, the centerline segmented model 1110 includes several branch points, some of which are highlighted for visibility. The branch points A, B, C, D, and E are shown at each of several of the branch points. The branch point A may represent the point in the model 1110 at which the trachea divides into the left and right principal bronchii. The right principal bronchus may be identified in the centerline segment model 1110 as being located between branch points A and B. Similarly, secondary bronchii are identified by the branch points B and C and between the branch points B and E. Another generation may be defined between branch points C and D. Each of these generations may be associated with a representation of the diameter of the lumen of the corresponding passageway. In some embodiments, the centerline model 1110 may include an average diameter value of each segmented generation. The average diameter value may be a patient-specific value or a more general value derived from multiple patients. Additionally, the centerline model 1110 include terminal points, of which exemplary terminal points F, G, and H are labeled in FIG. 12C. The terminal points F, G, and H indicate the limits of the results of the segmentation process. As seen in FIG. 12C, the centerline model 1110 does not extend beyond the unsegmented portions 1108 to the target 1104.

Figure 12D:
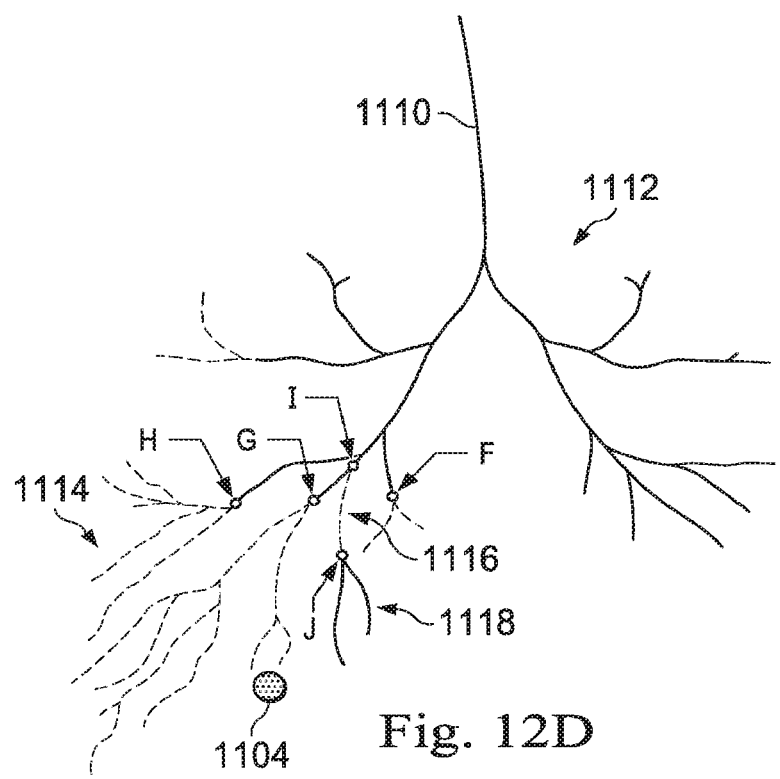

As discussed above in connection with operation 506 of the method 500 of FIG. 5A, the operator O may provide input via the input devices 130 or another operator input device that can be used by the control system 112 to augment the centerline model 1110 as shown in FIG. 12D. FIG. 12D shows an augmented model 1112. The augmented model 1112 includes the centerline model 1110 and an input-based model 1114. Described in connection with operation 506, the operator O may provide navigational directions, via the input devices 130, to virtually navigate within the image space and beyond the centerline segmented model 1110, while visualizing at least some of the image data 1102, such as voxels having a Hounsfield value associated with the bronchial walls 706. According to the received virtual movements, the control system 112 may track and record the movements to identify unsegmented portions of the anatomic passageways to extend centerline segmented model 1110 to create the input-based model 1114.

Additionally, some embodiments of the input devices 130 of FIG. 1 may permit the operator O to "draw" on a drawing tablet or on the display system 110, which may be a touchscreen, to define a line or pathway. The drawn line may be added to the centerline model 1110 to generate the augmented model 1112. For example, the operator O may draw lines on each of multiple views of the image data, such as the cross-sectional planes shown in FIGS. 6A-C. The control system 112 may process the multiple lines to generate a three-dimensional line to add to the centerline model 1110. In some processes, the operator O may be able to select one of the terminal points F, G, or H. The operator O may then be able to select an interior perspective view to be able to virtually navigate within the anatomical passageways to generate an input-based model or model portion beginning from the selected terminal point. Alternatively or additionally, the operator O may be presented with multiple cross-sectional planes of the image data on which to draw multiple two-dimensional lines which are then resolved to a single three-dimensional line to generate the input-based model 1114.

In other embodiments, the operator O may be able to select any point on the centerline model 1110 to be provided with virtual navigation or drawings with which to augment the centerline model. For example, the operator may select the intermediate point I on the centerline model 1110. The operator O may thereafter virtually navigate starting at the point I and draw a line extending from the point I to generate input-based line 1116. The operator O may provide an additional input indicating the end of the input-based line 1116, which is shown as terminal point J. After the operator has ended the input-based line 1116, the operator may request that the control system 112 attempt to segment the image data 1102. A segmentation process may begin at the terminal point J and automatically segment the image data 1102 to generate the centerline model portion 1118.

Combinations of these approaches may be used to generate a complete or partial model of the anatomic passageways based user interactions with the image data 1102. In some embodiments, combinations of segmentation-based modeling techniques and non-segmentation-based modeling techniques (such as virtual navigation or centerline drawing) may be used to generate a model, like the augmented model 1112, which can then be registered to a medical instrument inserted within the patient anatomy during a medical procedure. By registering the augmented model 1112 with the medical instrument, such as the elongate device 202 of FIGS. 2A and 2B, the image data associated with the model 1112 and the elongate device 202 may be brought into a common frame of reference for use in the image-guided medical procedure. Subsequently, a graphical representation of the registered elongate device 202 may be presented in the display system 110 along with the registered image data.

In other embodiments, the segmented model 1106 may be used to produce the centerline segment model 1110 or another suitable model including a cloud, set, or collection of points. When the segmented model 1106 comprises a mesh representing the internal surfaces of one or more passageways, a subset of vertices of a mesh as represented in a stored data file including the model 1106 may be used. Alternatively, a geometric center of the mesh or surface may be used to represent volumes or the passageways in the segmented model 1106.

In some embodiments, the centerline segmented model 1110 is represented in data as a cloud, set, 3D model, or collection of points in three-dimensional space, rather than as continuous lines. After the centerline segmented model 1110 is generated and stored in data as the set of points, the centerline segmented model 1110 may be retrieved from data storage for use in an image-guided surgical procedure. In order to use the centerline segmented model 1110 in the image-guided surgical procedure, the model 1110 may be registered to associate the modeled passageways in the model 1110 with the patient's actual anatomy as present in a surgical environment. Use of the model 1110 in point set registration includes using the set of points derived from or that make up the model 1110. Additionally, the augmented model 1112, including the portions derived from virtual navigation or from drawing may be represented as a set of points for use in a point set registration algorithm.

Referring now to FIG. 13, shown therein is an exemplary user interface 1200 as rendered in a display 1202. The display 1202 may be part of, or may be, the display system 110 of FIG. 1. User interface 1200 includes a main view 1204 in which image data may be rendered. As shown in FIG. 12, the main view 1204 includes an interior perspective of an anatomic passageway from for example, the point of view of a device, included in the preoperative or intraoperative three-dimensional image data. The user interface 1200 further includes ancillary views 1206, which may include one or more displays of the image data. As shown in FIG. 13, the ancillary views include three two-dimensional slices of CT image data. In some embodiments, the main view 1204 and the ancillary views 1206 may be displayed on separate display screens.

As depicted in FIG. 13, the user interface 1200 is in a virtual navigation mode, and so includes an internal perspective view in the main view 1204 and the three two-dimensional slices in the ancillary views 1206. At right, the user interface 1200 includes user interface options 1208, which includes virtual navigation options 1210, drawing options 1220, and filter selections 1230.

The virtual navigation options 1210 include user interface elements 1212A, 1212B, and 1212C. By selecting the begin navigation element 1212A, the operator O may begin virtual navigation, such that navigation inputs are recorded for assembly as a path to generate a model like the input-based model 1114. By selecting the pause navigation element 1212B, the operator O may temporarily stop the recording of virtual navigation and the operator O may move within the three-dimensional image space without having the navigation inputs recorded. By selecting the resume navigation element 1212C, the operator O may be able to resume recording the navigation inputs for assembly like the model 1114. In some embodiments, the perspective (i.e., position and orientation within the three-dimensional image data) may selectively return to the last recorded perspective or the perspective may remain wherever it is after the unrecorded navigation.

The drawing mode options 1220 may be used when the operator O intends to a draw a line or pathway to generate or add to a line-based model of the anatomical passageways. In some embodiments, when the user selects an element from the drawing mode options 1220 the main view 1204 may be populated with a first two-dimensional view of the image data, then a second two-dimensional view, then a third two-dimensional view in series, after the operator O draws on each view. The operator O may draw on the display 1202 when the display 1202 is a touch screen display. In other embodiments, the operator O may use a mouse, a keyboard or another input mechanism to draw lines on multiples perspectives of the image data, which are then combined to generate a three-dimensional line, or curve, that can be included in a line-based model of the anatomical passageways.

Additionally, the user interface options 1208 include the filter options 1230. The user interface elements included in the filter selections 1230 may be based on a workflow for example, if the operator O uses the input devices 130 to communicate to the control system 112 that the procedure to be performed is a lung biopsy, the control system 112 may pre-populate the filter selections 1230 with user interface elements appropriate for a lung biopsy. For example, as illustrated, the filter selections 1230 include a bronchial walls element 1232A, an adjacent vessels element 1232B, and a bone element 1232C. The operator O may interact with the elements 1232A-C to toggle the display of CT data having Hounsfield values in associated ranges on and off. In some embodiments, the elements 1232A-C may each have a continuous input element that provides for varying degrees of transparency/opacity. Additionally, when the procedure being performed does not involve the lungs, the filter selections 1230 may include other elements.

Many different variations of the user interface 1200 are included within the scope of this disclosure. For example other user interface options and user interface controls may be included, such as an option to segment the image data or to continue segmenting the image data as discussed above in connection with FIGS. 12A-D.

Referring now to FIG. 14, shown therein is a flowchart of a method 1300 of providing image-based guidance during a minimally-invasive medical procedure. Like other methods described herein, the method 1300 is depicted as a series of operations. Embodiments of the method 1300 may include additional or alternative operations and/or may omit one or more of the enumerated operations. Some embodiments of the method 1300 may include instructions readable by the control system 112 or the processing device 114 to cause the control system 112 to perform the operations of the method 1300.

Some embodiments of the method 1300 may begin at operation 1302, in which a processing device, such as the processing device 114 of the control system 112, receives three-dimensional image data of at least a portion of patient anatomy. For example, the control system 112 may receive CT image data showing the torso of the patient P, including patient P's lungs. The image data may be obtained from another portion of the patient's anatomy in other embodiments.

At operation 1304, the processing device may register the three-dimensional image data with a surgical environment. In some embodiments, the image data may be registered with the surgical environment by registering a fiducial marker contained within the image data to a corresponding fiducial marker in the surgical environment. At operation 1306, the processing device registers a medical instrument coupled to the teleoperational medical system with the surgical environment, for example by driving the medical instrument within the portion of patient anatomy, and capturing measured points associated with a tracked position of the medical instrument. In some embodiments, the operations 1304 and 1306 may be combined into a single registration operation that directly registers the three-dimensional image data with the medical instrument. The process of registration included in the method 1300 may include operations of generating a model from the received image data, or generating a portion of such a model based on tracked virtual movement commands of the operator O within the space defined by the image data, as described above in connection with the method 500 of FIG. 5A. After operations 1304 and 1306, information obtained using the medical instrument can be associated by the control system 112 with the three-dimensional image data. For example, the control system 112 may cause a live view obtained by camera at the distal end of the medical instrument to be displayed alongside a portion of the image data as viewed from a perspective of the distal end of the medical instrument. For example, the main view 1204 of the user interface 1200 may include a split view with the live feed from the camera and the perspective view of the image data.

At operation 1308, the processing device may apply a filter to the three-dimensional image data to alter a rendering of one or more voxels of the three-dimensional image data. For example, when the image data is displayed from a perspective of the distal end of the medical instrument, some portions of the image data may be filtered to provide a desired presentation of the image data. For example, the image data may be filtered according to the Hounsfield value associated with the voxel. The operator O may selectively cause, or the control system 112 may automatically cause, certain tissues to be displayed entirely transparently or partially transparently to enable certain aspects to be visualized more easily. For example, voxels having a Hounsfield value associated with air may be rendered transparently, while the tissue defining the bronchial passageways is rendered semi-transparently, and the blood vessels surrounding the bronchial passageways may be rendered opaquely. As another example, a target contained within the image data may be rendered as an opaque mass, while all of the tissues are rendered semi-transparently. Other combinations may be used to permit the operator O to visualize information judged to be most useful in any particular situation. Additionally, filters may provide for different coloration in addition to degrees of transparency for certain tissues.

At operation 1310, the processing device may render the three-dimensional image data in a display from a perspective associated with the medical instrument. As noted, this may be done in a first portion of a display screen or in a first display screen, while live video from the same perspective or from a different perspective is provided in a second portion of the display screen or in a second display screen. In this way, if the live video from the medical instrument becomes obstructed, the CT data may be used by the operator O for continued navigation. Additionally, the operator O may make comparisons between the tissues, fluids, etc., shown in the live view and the same subjects as included in the image data. Other imaging modalities, intraoperative or pre-operative, may be compared with the CT image data in other embodiments. The operator O may make selections in a user interface like the user interface 1200 of FIG. 12 to provide selections of tissue types and/or to receive rendering settings associated with each of the tissue types to the control system 112. For example, when the operator O selects the bronchial walls element 1232A, the user interface 1200 may present additional user interface options, such as sliders or entry fields, whereby the operator O may enter a transparency setting and/or a color setting associated with the bronchial walls element 1232A. The settings may then be applied to the voxel's associated with the Hounsfield value of the bronchial walls.

In some embodiments of the method 1300, when the control system 112 detects a change in position of the medical instrument, the perspective from which the image data is viewed may be updated to reflect the change in position of the medical instrument, such that the navigation commands transmitted to steer/position the medical instrument are simultaneously utilized for virtual navigation of the image data.

Embodiments of the present disclosure may provide for significant improvements in image-guided medical procedures. For example, some embodiments may permit the use of lower resolution CT scans to be used in generating a model of patient anatomy. By improving the usefulness of such lower resolution CT scans, patient exposure to the radioactive imaging agents used to obtain the image data may be decreased. Some embodiments may permit use of both segmentation and user input to generate a hybrid model of patient anatomy, which may result in improved efficiency and accuracy in generating such anatomic models that permit registration. Additionally, embodiments of the present disclosure may facilitate simultaneously viewing the image data along with live video data during a medical procedure.

Embodiments of the methods and systems described herein include computer readable storage media, such as CD-ROMs, DVDs, flash memory, and other storage medium, having machine-readable instructions stored thereon. The processing device, such as a processing device included in the control system 112 of FIG. 1. Additional embodiments of the present disclosure include systems, such as a workstation, having one or more processing devices (such as a CPU and GPU) and a memory storing instructions that, when read by the processing device, cause the system to perform an embodiment of one of the methods 400, 500, and 1300. Additionally, features described with respect to the various embodiments of the present disclosure may be combined. For example, operations discussed with respect to method 1300 may be included in embodiments of the method 500. Furthermore, variations and modifications that are apparent to one of ordinary skill in the art may be made to embodiments of the present disclosure without departing from the scope thereof. While some more specific embodiments have been described with respect to the lungs of the patient, other anatomic passageways, structures, and organs may be imaged, registered, and be observed and treated by utilizing embodiments of this disclosure. Such organs may include the heart, the digestive tract, the kidneys, and others. Accordingly, the scope and spirit of the disclosure are best understood by reference to the following claims.

What is claimed is:

1. A method comprising:
receiving, by a medical imaging system having at least one processing device, three-dimensional image data of a patient anatomy;
filtering the three-dimensional image data to display a portion of the three-dimensional image data that is associated with the patient anatomy;
receiving, at the at least one processing device, input from an operator input device, the input comprising navigational directions for virtual movement within a space defined by the three-dimensional image data;
tracking the virtual movement;
defining a tracked pathway based on the tracked virtual movement; and
generating a model of the patient anatomy based on the tracked pathway, wherein the model of the patient anatomy is a line model comprising one or more lines based on the tracked pathway.

2. The method of claim 1, further comprising:
identifying a target in the three-dimensional image data;
determining a vector extending between a viewpoint of the three-dimensional image data in space and the target; and
rendering a user interface element representing the vector on a display displaying a rendering of the three-dimensional image data to provide navigational guidance.

3. The method of claim 1, further comprising:
identifying a target in the three-dimensional image data;
determining a first subset of modeled passageways that permit access to the target; and
rendering a first user interface element indicating that a first modeled passageway is excluded from the first subset of modeled passageways.

4. The method of claim 1, further comprising:
identifying a target in the three-dimensional image data;
determining a first subset of modeled passageways that permit access to the target; and
rendering a first user interface element indicating that a first modeled passageway is included within the first subset of modeled passageways.

5. The method of claim 4, further comprising:
blocking virtual navigation beyond a location in the three-dimensional image data associated with the rendered first user interface element.

6. A system for processing medical images, the system comprising:
a memory configured for storing three-dimensional image data of at least a portion of a patient anatomy;
a processing device in communication with the memory, the processing device configured to execute instructions to perform operations comprising:
receiving the three-dimensional image data;
filtering the three-dimensional image data;
generating a display of a portion of the three-dimensional image data associated with the patient anatomy;
receiving input from an operator input device, the input comprising navigational directions for virtual movement within an image space defined by the portion of the three-dimensional image data;
defining a tracked pathway by tracking the virtual movement; and
generating a model of the patient anatomy based on the tracked pathway, wherein the model of the patient anatomy is a line model comprising one or more lines based on the tracked pathway.

7. The system of claim 6, wherein receiving the input from the operator input device comprises:
receiving a first input associated with virtual movement in a first perspective of the three-dimensional image data;
receiving a second input associated with virtual movement in a second perspective of the three-dimensional image data; and
combining the first and second inputs associated with the first and second perspectives to generate the model.

8. The system of claim 6, wherein the operator input device is a three-dimensional input device configured to process operator motion in three dimensions into the model.

9. The system of claim 6, wherein the processing device is further configured to execute instructions to perform rendering of a graphical user interface in a display in communication with the processing device.

10. The system of claim 9, wherein rendering the graphical user interface comprises rendering the filtered three-dimensional image data from a perspective internal to the three-dimensional image data or from a perspective external to the three-dimensional image data.

11. The system of claim 9, wherein rendering the graphical user interface comprises rendering the filtered three-dimensional image data from a perspective external to the three-dimensional image data.

12. The system of claim 11, wherein the receiving input from the operator input device comprises receiving one or more drawing inputs from the operator input device, the one or more drawing inputs representing one or more three-dimensional lines drawn on one or more views of the three-dimensional image data by an operator.

13. The system of claim 9, wherein the operations further comprise displaying a plurality of filter selections and receiving a selection of at least one of the plurality of filter selections, wherein rendering the graphical user interface comprises rendering a filtered portion of the three-dimensional image data according to the selection of at least one of the plurality of filter selections.

14. The system of claim 9, wherein the operations further comprise receiving a selection of a user interface element from an operator, the selection indicating a virtual navigation input mode or a drawing input mode.

15. The system of claim 9, wherein the operations further comprise displaying a generated pathway and the three-dimensional image data in the display.

16. The system of claim 15, wherein the generated pathway and the three-dimensional image data are displayed simultaneously.

17. The system of claim 6, wherein the processing device is configured to perform the filtering of the three-dimensional image data according to a density value to identify a feature in the received three-dimensional image data.

18. The system of claim 6, wherein the processing device is configured to perform the filtering of the three-dimensional image data according to different density values to identify different areas of the received three-dimensional image data.

19. The system of claim 6, wherein the processing device is configured to perform the filtering of the three-dimensional image data according to a density value to isolate air from an anatomical feature in the received three-dimensional image data.

\* \* \* \* \*

UNITED STATES PATENT AND TRADEMARK OFFICE
CERTIFICATE OF CORRECTION

| | |
|---|---|
| PATENT NO. | : 11,547,490 B2 |
| APPLICATION NO. | : 16/349073 |
| DATED | : January 10, 2023 |
| INVENTOR(S) | : Bai Wang and Tao Zhao |

It is certified that error appears in the above-identified patent and that said Letters Patent is hereby corrected as shown below:

In the Specification

Column 13, Line 41, change "lose-close" to -- low-dose --

Signed and Sealed this
Seventh Day of March, 2023

Katherine Kelly Vidal
*Director of the United States Patent and Trademark Office*